(12) United States Patent
Bakaletz et al.

(10) Patent No.: US 8,741,304 B2
(45) Date of Patent: *Jun. 3, 2014

(54) **CHIMERIC VACCINE FOR *HAEMOPHILUS INFLUENZAE*-INDUCED DISEASE**

(75) Inventors: Lauren O. Bakaletz, Hilliard, OH (US); Robert S. Munson, Jr., Columbus, OH (US)

(73) Assignee: Nationwide Children's Hospital

( * ) Notice: Subject to any disclaimer, the term of this patent is extended or adjusted under 35 U.S.C. 154(b) by 0 days.

This patent is subject to a terminal disclaimer.

(21) Appl. No.: 13/608,500

(22) Filed: Sep. 10, 2012

(65) Prior Publication Data

US 2013/0064828 A1 Mar. 14, 2013

Related U.S. Application Data

(60) Continuation of application No. 12/898,287, filed on Oct. 5, 2010, now Pat. No. 8,263,363, which is a division of application No. 11/994,830, filed as application No. PCT/US2006/026183 on Jul. 5, 2006, now Pat. No. 7,811,591.

(60) Provisional application No. 60/697,642, filed on Jul. 8, 2005, provisional application No. 60/801,835, filed on May 19, 2006.

(51) Int. Cl.
*A61K 39/02* (2006.01)
*C12P 21/04* (2006.01)
*C12N 15/09* (2006.01)
*C07K 14/195* (2006.01)

(52) U.S. Cl.
USPC ... 424/190.1; 435/69.1; 435/69.7; 435/320.1; 530/350

(58) Field of Classification Search
None
See application file for complete search history.

(56) References Cited

U.S. PATENT DOCUMENTS

| 5,766,608 A * | 6/1998 | Kolattukudy et al. | 424/256.1 |
| 5,843,464 A | 12/1998 | Bakaletz et al. | |
| 6,268,171 B1 | 7/2001 | Meyer et al. | |
| 6,506,581 B1 | 1/2003 | Fleischmann et al. | |
| 7,811,591 B2 * | 10/2010 | Bakaletz et al. | 424/256.1 |

FOREIGN PATENT DOCUMENTS

| WO | WO-99/64067 | 12/1999 |
| WO | WO-2005/063802 | 7/2005 |

OTHER PUBLICATIONS

Anderson et al., Human serum activities against *Hemophilus influenzae*, Type B. *J. Clin. Invest.* 51: 31-8 (1972).
Bakaletz et al., Demonstration of type IV pilus expression and a twitching phenotype by *Haemophilus influenzae*. *Infect. Immun.* 73(3): 1635-43 (2005).
Bakaletz et al., Evidence for transduction of specific antibodies into the middle ear of parenterally immunized chinchillas after an upper respiratory infection with adenovirus. *Clin. Diag. Lab. Immunol.* 4(2): 223-5 (1997).
Bakaletz et al., Frequency of fimbriation of nontypable *Haemophilus influenzae* and its ability to adhere to chinchilla and human respiratory epithelium. *Infect. Immun.* 56(2): 331-5 (1988).
Bakaletz et al., Modeling adenovirus type 1-induced otitis media in the chinchilla: Effect on ciliary activity and fluid transport function of eustachian tube mucosal epithelium. *J. Infect. Dis.* 168: 865-72 (1993).
Bakaletz et al., Protection against development of otitis media induced by nontypeable *Haemophilus influenzae* by both active and passive immunization in a chinchilla model of virus-bacterium superinfection. *Infect. Immun.* 67(6): 2746-62 (1999).
Bakaletz et al., Relative immunogenicity and efficacy of two synthetic chimeric peptides of fimbrin as vaccinogens against nasopharyngeal colonization by nontypeable *Haemophilus influenzae* in the chinchilla. *Vaccine*, 15(9): 955-61 (1997).
Baldwin et al., Effects of otitis media on child development. *Am. J. Otol.* 14: 601-4 (1993).
Bardy et al., Prokaryotic motility structures. *Microbiol.* 149: 295-304 (2003).
Barenkamp et al., Outer membrane protein and biotype analysis of pathogenic nontypable *Haemophilus influenzae*. *Infect. Immun.* 36(2): 535-40 (1982).
Berman et al., Theoretical cost effectiveness of management options for children with persisting middling ear effusions. *Pediatrics.* 93: 353-63 (1994).
Black et al., Efficacy, safety and immunogenicity of heptavalent pneumococcal conjugate vaccine in children. *Ped. Infect. Dis. J.* 19(3): 187-95 (2000).
Bright et al., The prevalence of tympanostomy tubes in children in the United States. *Am. J. Public Health.* 83: 1026-8 (1993).
Catlin et al., The type B capsulation locus of *Haemophilus influenzae*: Map location and size. *J. Microbiol.* 70: 411-22 (1972).
Cimons et al., Lurid reports obscure reality of strep A outbreaks. *ASM News.* 60: 527-30 (1994).
Clemans et al., Comparative analysis of *Haemophilus influenzae* hifA (philin) genes. *Infect. Immun.* 66(2): 656-63 (1998).
Coleman et al., Chemically defined media for growth of *l Haemophilus influenzae* strains. *J. Clin. Micro.* 41: 4408-10 (2003).
Coleman et al., Molecular cloning, expression, and sequence of the Pilin gene from nontypeable *Haemophilus influenzae* M37. *Infect. Immunity.* 59: 1716-22 (1991).
Daines et al., *Haemophilus influenzae* Rd KW20 has virulence properties. *J. Med. Microbiol.* 52: 277-82 (2003).
Darzin et al., Molecular genetic analysis of type-4 pilus biogenesis and twitching motility using *Pseudomonas aeruginosa* as a model system—a review. *Gene.* 192: 109-15 (1997).

(Continued)

*Primary Examiner* — Padma V Baskar
(74) *Attorney, Agent, or Firm* — Marshall, Gerstein & Borun LLP

(57) ABSTRACT

The invention described herein relates to a chimeric protein comprising the NTHi twitching pilus major subunit protein (PilA) presenting a portion of the NTHi OMP P5 protein. The invention provides for vaccine compositions comprising the recombinant chimeric protein and methods of eliciting an immune response using the recombinant chimeric proteins of the invention.

6 Claims, 1 Drawing Sheet

(56) References Cited

OTHER PUBLICATIONS

DeMaria, et al., Immunization with Outer Membrane Protein P6 from Nontypeable *Haemophilus influenzae* Induces Bactericidal Antibody and Affords Protection in the Chinchilla Model of Otitis Media. *Infection and Immunity*, 64(12): 5187-5192 (Dec. 1996).

Devereux et al., A comprehensive set of sequence analysis programs for the VAX. *Nucl Acids. Res*. 12(1): 387-395 (1984).

Dougherty et al., Identification of *Haemophilus influenzae* Rd transformation genes using cassette mutagenesis. *Microbiology*. 145: 401-9 (1999).

Dougherty et al., The type 4 fimbrial subunit gene of *Pasteurella multocida*. *Vet. Microbiol*. 72: 79-90 (2000).

Ehrlich et al., Mucosal biofilm formation of middle-ear mucosa in the chinchilla model of otitis media. *JAMA*. 287: 1710-5 (2002).

Eskola et al., Efficacy of a pneumococcal conjugate vaccine against acute otitis media. *N. Engl. J. Med*. 344(6): 403-9 (2001).

Eskola et al., Potential of bacterial vaccines in the prevention of acute otitis media. *Ped. Infect. Dis. J*. 19(5): S72-8 (2000).

Fleischmann et al., Whole-genome random sequence and assembly of *Haemophilus influenzae* Rd. *Science*,269: 496-512 (1995).

Friedrich et al., Molecular analyses of the natural transformation machinery and identification of pilus structures in the extremely thermophilic bacterium *Thermus termophilus* strain HB27. *Appl. Environ. Microbiol*. 68: 745-55 (2002).

Friedrich et al., Pilin-like proteins in the extremely thermophilic bacterium *Thermus thermophilus* HB27: Implications in competence for natural transformation and links to type IV pilus biogenesis. *Appl. Environ. Microbiol*. 69: 3695-700 (2003).

Fussenegger et al., Tranformation competence and type-4 pilus biogenesis in *Neisseria gonorrhoeae*—a review. *Gene*. 192: 125-34 (1997).

Genbank Accession No. P45285, Peptide transport periplasmic protein sapA precursor, Sep. 13, 2005.

Genbank Accession No. U32837, *Haemophilus influenzae* Rd KW20 section 152 of 163 of the complete genome, Jun. 2, 2004.

Giebink, Immunology: Promise of New Vaccines, *Ped. Infect Dis. J*., 13(11): 1064-1068 (1994).

Gilsdorf et al., Role of pili in *Haemophilus influenzae* adherence to, and internalization by, respiratory cells. *Pediatr. Res*. 39: 343-8 (1996).

Gilsdorf et al., Role of pili in *Haemophilus influenzae* adherence and colonization. *Infect. Immun*. 65: 2997-3002 (1997).

Holmes, et al., Adherence of Non-Typeable *Haemophilus influenzae* Promotes Reorganization of the Actin Cytoskeleton in Human or Chinchilla Epithelial Cells in vitro, *Microbial Pathogenesis*, 23: 157-166 (1997).

Hunter et al., Identification of hearing loss in children with otitis media. *Ann. Otol. Rhinol. Laryngol. Suppl*. 163: 59-61 (1994).

Jansen et al., Immunotoxins: Hybrid molecules combining high specificity and potent cytotoxicity. *Immun. Rev*. 62: 185-216 (1982).

Jesaitis et al., Compromised host defence on *Pseudomonas aeruginosa*biofilms: Characterization of neutrophil and biofilm interactions. *J. Immunol*. 171: 4329-39 (2003).

Kaplan et al., Overall cost in the treatment of otitis media. *Pediatr. Infect. Dis. J*. 16: S9-11 (1997).

Karma et al., Immunological Aspects of Otitis Media: Present Views on Possibilities of Immunoprophylazis of Acute Otitis Media in Infants and Children, *Int. J. Pediat. Otorhinolaryngology*, 32 (Suppl.): S127-S134 (1995).

Karudapuram et al., The *Haemophilus influenzae* dprABC genes constitute a competence-inducible operon that requires the product of the tfoX(sxy) gene for transcriptional activation. *J. Bacteriology*. 179(15): 4815-20 (1997).

Keizer et al., Structure of a pilin monomer from *Pseudomonas aeruginosa*. *J. Biol. Chem*. 276: 24186-93 (2001).

Kennedy et al., Passive transfer of antiserum specific for immunogens derived from a nontypeable *Haemophilus influenzae* adhesin and lipoprotein D prevents otitis media after heterologous challenge. *Infect. Immun*. 68(5): 2756-65 2000).

Klausen et al., Biofilm formation by *Pseudomonas aeruginosa* wild type, flagella and type IV pili mutants. *Mol. Microbiol*. 48: 1511-24 (2003).

Klausen et al., Involvement of bacterial migration in the development of complex multicellular structures in *Pseudomonas aeruginosa* biofilms. *Mol. Microbiol*. 50: 61-8 (2003).

Klein, Role of nontypeable *Haemophilus influenzae* in pediatric respiratory tract infections. *Pedriatr. Infect. Dis. J*. 16: S5-8 (1997).

Klein, the burden of otitis media. *Vaccine*, 19(Suppl. 1): S2-8 (2001).

Kyd et al., Potential of a novel protein, OMP26, from nontypeable *Haemophilus influenzae* to enhance pulmonary clearance in a rat model. *Infect. Immun*. 66: 2272-8 (1998).

Lopez-Solanilla et al., Inactivation of the sapA to sapF locus of *Erwinia chrysanthemi* reveals common features in plant and animal bacterial pathogenesis. *Plant Cell*, 10: 917-24 (1998).

Mason et al., Nontypeable *Haemophilus influenzae* gene expression induced in vivo in a chinchilla model of otitis media. *Infect. Immunol*. 71: 3454-62 (2003).

Matteucci et al., Synthesis of deoxyoligonucleotides on a polymer support. *J. Am. Chem. Soc*. 103:3185 (1981).

Mattick, Type IV pili and twitching motility. *Annu. Rev. Microbiol*. 56: 289-314 (2002).

McCoy et al., Identification of *Proteas mirabilis* with Increased Sensitivity AntiMicrobial Peptides. *Antimicrob. Agents Chemother*. 45(7): 2030-7 (2001).

Merz et al., Pilus retraction powers bacterial twitching motility. *Nature*, 407: 98-102 (2000).

Mhlanga-Mutangadura et al., Evolution of the major pilus gene cluster of *Haemophilus influenzae*. *J. Bacteriol*. 180(17): 4693-703 (1998).

Mudannayake et al., Whole genome analysis of gene expression changes during competence development in *Haemophilus influenzae*. *Abstracts of the General Meeting of the American Society for Microbiology*. 103: D-001 (2003).

Musser et al., Genetic relationships of serologically nontypable and serotype b strains of *Haemophilus influenzae*. *Infect. Immun*. 52(1): 183-91 (1986).

Novotny et al., Epitope mapping of the outer membrane protein P5-homologous fimbrin adhesin of nontypeable *Haemophilus influenzae*. *Infect.Immun*. 68(4): 2119-28 (2000).

Novotny et al., The fourth surface-exposed region of the outer membrane protein P5-homologous adhesion of nontypable *Haemophilus influenzae* is an immunodominant but nonprotective decoying epitope. *J. Immunol*. 171: 1978-83 (2003).

O'Toole et al., Flagellar and twitching motility are necessary for *Pseudomonas aeruginosa* biofilm development. *Mol. Microbiol*. 30: 295-304 (1998).

Paap, Management of otitis media with effusion in young children. *Ann. Pharmacother*. 30(11): 1291-7 (1996).

Parra-Lopez et al., A *Salmonella* protein that is required for resistance to antimicrobial peptides and transport of potassium. *EMBO J*. 13(17): 3964-72 (1994).

Parra-Lopez et al., Molecular genetic analysis of a locus required for resistance to antimicrobial peptides in *Salmonella typhimurium*. *EMBO J*. 12(11): 4053-4062 (1993).

Perez-Casal et al., Mry, a trans-acting positive regulator of the M protein gene of *Streptococcus pyogenes* with similarity to the receptor proteins of two-component regulatory systems. *J. Bacteriol*. 173: 2617-24 (1991).

Poje et al., *Haemophilus Influenzae* Protocols, Transformation of *Haemophilus influenzae*, Humana Press Inc., Toronto, pp. 57-70 (2003).

Poolman et al., Developing a nontypeable *Haemophilus influenzae* (NTHi) vaccine. *Vaccine*, 19: S108-15 (2001).

Risberg et al., Structural analysis of the lipopolysaccharide oligosaccharide epitopes expressed by a capsule-deficient strain of *Haemophilus influenzae* Rd. *Eur. J. Biochem*. 261: 171-80 (1999).

Ruffolo et al., Identification, purification, and characterization of the type 4 fimbriae of *Pasteurella multocida*. *Infect. Immun*. 65: 339-43 (1997).

Semmler et al., A re-examination of twitching motility in *Pseudomonas aeruginosa*. *Microbiology*. 145: 2863-73 (1999).

(56) References Cited

OTHER PUBLICATIONS

Skerker et al., Direct observation of extension and retraction of type IV pili. *Proc. Natl. Acad. Sci. USA.* 98: 6901-4 (2001).
Snow, Progress in the prevention of otitis media through immunization. *Otology & Neurotology,* 23(1): 1-2 (2002).
Spinola et al., Epidemiology of colonization by nontypable *Haemophilus influenzae* in children: a longitudinal study. *J. Infect. Dis.* 154(1): 100-9 (1986).
St. Geme III, Molecular and cellular determinants of non-typeable *Haemophilus influenzae* adherence and invasion. *Cell Microbiol.* 4: 191-200 (2002).
Stevenson et al., Cloning and characterisation of type 4 fimbrial genes from *Actinobacillus pleuropneumoniae. Vet. Microbiol.* 92:121-34 (2003).
Strom, Structure-function and biogenesis of the type IV pili. *Annu. Rev. Microbiol.* 47: 565-96 (1993).
Suzuki et al., Synergistic effect of adenovirus type 1 and nontypeable *Haemophilus influenzae* in a chinchilla model of experimental otitis media. *Infect. Immun.* 62(5): 1710-8 (1994).
Swiss Prot Accession No. P31768, Jul. 1, 1993.
Swiss Prot Accession No. P31769, Jul. 1, 1993.
Swiss Prot Accession No. P31770, Jul. 1, 1993.
Swiss Prot Accession No. P31771, Jul. 1, 1993.
Swiss Prot Accession No. P31772, Jul. 1, 1993.
Swiss Prot Accession No. P31773, Jul. 1, 1993.
Teele et al., Otitis media in infancy and intellectual ability, school achievement, speech, and language at age 7 years. *J. Infect. Dis.* 162: 685-94 (1990).
Tonjum et al., The pilus colonization factor of pathogenic neisserial species : organelle biogenesis and structure/function relationships—a review. *Gene,* 192: 155-63 (1997).
UniProt Database Accession No. Q5D8E3_HAEIN, PilA, *Haemophilus influenzae,* Mar. 29, 2005.
Wall et al., Type IV pili and cell motility. *Mol. Microbiol.* 32:1-10 (1999).
Watson et al., Identification of a gene, pilF, required for type 4 fimbrial biogenesis and twitching motility in *Pseudomonas aeruginosa. Gene,* 180: 49-56 (1996).
Wolfgang et al., Components and dynamics of fiber formation define a ubiquitous biogenesis pathway for bacterial pili. *EMBO J.* 19: 6408-18 (2000).
Zhang et al., Identification of type 4 fimbriae in *Actinobacillus pleuropneumoniae. FEMS Microbiol Lett.* 189: 15-8 (2000).
Zwahlen et al., Participation of complement in host defense against cCapsule-deficient *Haemophilus influenzae. Infect. Immun.* 42: 708-15 (1983).
International Search Report, European Patent Office, PCT/US2006/026183, dated Dec. 27, 2006.

\* cited by examiner

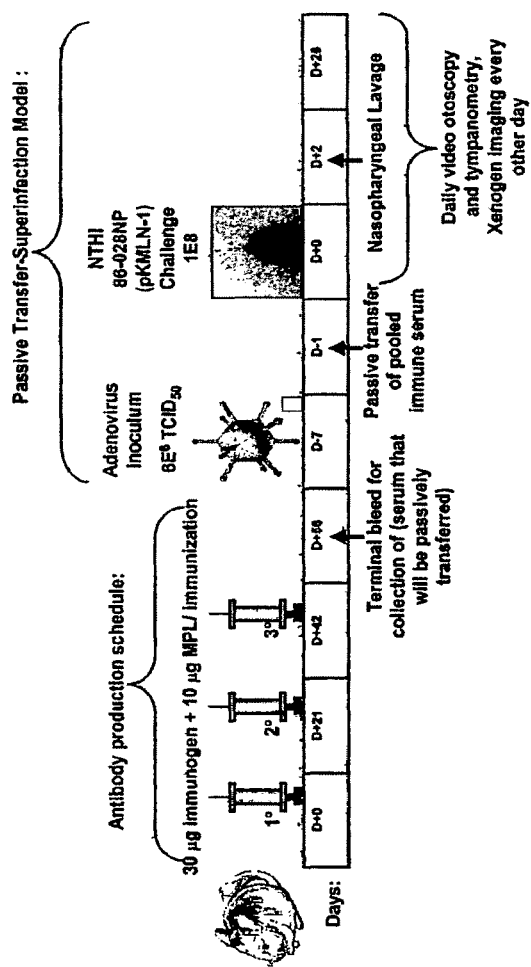

CHIMERIC VACCINE FOR *HAEMOPHILUS INFLUENZAE*-INDUCED DISEASE

This application is a divisional of U.S. application Ser. No. 12/898,287, filed Oct. 5, 2010, now U.S. Pat. No. 8,263,363, which is a divisional of U.S. application Ser. No. 11/994,830, filed Jul. 9, 2008, now U.S. Pat. No. 7,811,591, which claims priority to U.S. Provisional Application No. 60/697,642 filed Jul. 8, 2005 and U.S. Provisional Application No. 60/801,835 filed May 19, 2006, all of which are incorporated by reference herein in its their entirety.

FIELD OF INVENTION

The invention described herein relates to a chimeric protein comprising the NTHi twitching pilus major subunit protein (PilA) presenting a portion of the NTHi OMP P5 protein. The invention provides for vaccine compositions comprising the chimeric protein and methods of eliciting an immune response using the chimeric proteins of the invention.

BACKGROUND

The clinical term for middle ear infections is otitis media (OM). According to Klein, *Vaccine*, 19 (Suppl. 1): S2-S8, 2000, OM is the most common reason for an ill child to obtain healthcare and for a child in the United States to receive antibiotics or undergo general anesthesia. Statistics indicate that 24.5 million physician office visits were made for OM in 1990, representing a greater than 200% increase over those reported in the 1980s. While rarely associated with mortality, the morbidity associated with OM is significant. Hearing loss is a common problem associated with this disease, often affecting a child's behavior, education and development of language skills (Baldwin, *Am. J. Otol.*, 14: 601-604, 1993; Hunter et al., *Ann. Otol. Rhinol. Laryngol. Suppl.*, 163: 59-61, 1994; Teele et al., *J. Infect. Dis.*, 162: 685-694, 1990). The socioeconomic impact of OM is also great, with direct and indirect costs of diagnosing and managing OM exceeding $5 billion annually in the U.S. alone (Kaplan et al., *Pediatr. Infect. Dis. J.*, 16: S9-11, 1997).

OM is thought to result from infectious, environmental and host genetics factors. Bacteria such as *Haemophilus influenzae*, *Streptococcus pneumoniae* and *Moraxella catarrhalis* are the most common infectious organisms in OM. Acute OM is a disease characterized by rapid onset and short duration of signs and symptoms of inflammation in the middle ear, while chronic OM refers to a condition that is defined by the relatively asymptomatic presence of fluid (or effusion) in the middle ear. However, in chronic OM, despite the absence of certain signs of acute infection (i.e., ear pain or fever), these abnormal middle ear fluids can persist for periods exceeding three months. Treatment of acute OM by antibiotic therapy is common, but multiple antibiotic-resistant bacteria have emerged in all three Genera of bacteria responsible for OM. Surgical management of chronic OM involves the insertion of tympanostomy tubes through the tympanic membrane of the ear while a child is under general anesthesia. While this procedure is commonplace (prevalence rates are ~1 million tubes inserted per year in the U.S. Bright et al., *Am. J. Public Health*, 83(7): 1026-8, 1993) and is highly effective in teens of relieving painful symptoms by draining the middle ear of accumulated fluids, it is invasive and carries incumbent risks (Berman et al., *Pediatrics*, 93(3):353-63, 1994; Bright et al., supra.; Cimons, *ASM News*, 60: 527-528; Paap, *Ann. Pharmacother.*, 30(11): 1291-7, 1996). There is thus a need for additional approaches to the management and, preferably, the prevention of OM.

OM vaccine development is most advanced for *S. pneumoniae*, the primary causative agent of acute OM (AOM), as evidenced by the recent approval and release of a seven-valent capsular-conjugate vaccine, PREVNAR® (Eskola and Kilpi, *Pediatr. Infect. Dis. J.* 16: S72-78, 2000). While PREVNAR® has been highly efficacious for invasive pneumococcal disease, coverage for OM has been disappointing (6-8%) with reports of an increased number of OM cases due to serotypes not included in the vaccine (Black et al., *Pediatr. Infect. Dis J*, 19: 187-195, 2000; Eskola et al., *Pediatr. Infect. Dis J.*, 19: S72-78, 2000; Eskola et al., *N. Engl. J. Med.*, 344: 403-409, 2001; Snow et al., *Otol. Neurotol.*, 23: 1-2, 2002).

*H. influenzae* is a gram-negative bacterium that, as noted above, plays a role in OM. Clinical isolates of *H. influenzae* are classified either as serotypes "a" through "f" or as non-typeable depending on the presence or absence, respectively, of type-specific polysaccharide capsules on the bacteria. A vaccine for *H. influenzae* type b has been developed. Like PREVNAR®, the type b *H. influenzae* vaccines target the polysaccharide capsule of this organism and thus the vaccine is comprised of capsule polysaccharide that has been conjugated to a protein carrier. Neither PREVNAR® or the type b *H. influenzae* vaccine have any efficacy for NTHi-induced respiratory tract diseases, including OM. Less progress has been made for a vaccine for non-typeable *H. influenzae* (NTHi) which causes approximately 20% of acute OM in children and predominates in chronic OM with effusion (Coleman et al., *Inf and Immunity*, 59(5), 1716-1722, 1991; Klein, *Pediatr. Infect. Dis J.*, 16, S5-8, 1997; Spinola et al., *J. Infect. Dis.*, 154, 100-109, 1986). NTHi can also cause pneumonia, sinusitis, septicemia, endocarditis, epiglottitis, septic arthritis, meningitis, postpartum and neonatal infections, postpartum and neonatal sepsis, acute and chronic salpingitis, pericardis, cellulitis, osteomyelitis, endocarditis, cholecystitis, intraabdominal infections, urinary tract infection, mastoiditis, aortic graft infection, conjunctitivitis, Brazilian purpuric fever, occult bacteremia and exacerbation of underlying lung diseases such as chronic bronchitis, bronchietasis and cystic fibrosis. A prototype NTHi isolate is the low passage isolate 86-028NP which was recovered from a child with chronic OM. This strain has been well characterized in vitro (Bakaletz et al., *Infect. Immun.*, 53: 331-5, 1988; Holmes et al., *Microb. Pathog.*, 23: 157-66, 1997) as well as in chinchilla OM models (Bakaletz et al., *Vaccine*, 15: 955-61, 1997; Suzuki et al., *Infect. Immun.*, 62: 1710-8, 1994; DeMaria et al., *Infect. Immun.*, 64: 5187-92, 1996). The NTHi strain 86-026NP was deposited with the American Type Culture Collection, 10801 University Blvd., Manassas, Va. 20110, on Oct. 16, 2001 and assigned accession no. PTA-4764. A contig set from the genome of stain 86-028NP can be found at Columbus Children's Research Institute Center for Microbial Pathogenesis web site.

Adherence and colonization are acknowledged first steps in the pathogenesis of *H. influenzae*-induced diseases. As such, *H. influenzae* express multiple adhesins including hemagglutinating pili, fimbriae and non-fimbrial adhesins (Gilsdorf et al., *Pediatr Res* 39, 343-348, 1996; Gilsdorf., Infect. Immun., 65, 2997-3002, 1997; and St. Geme III, *Cell. Microbiol.*, 4, 191-200, 2002). Notably, none of the adhesins described have previously been associated with a motility function. Moreover, *H. influenzae* do not express flagella which are also associated with motility. Twitching motility is a flagella-independent fowl of bacterial translocation over moist surfaces and occurs by extension, tethering, and then retraction of polar structures known as type IV pili (Bardy., *Microbiology*, 149, 295-304, 2003; Tonjum and Koomey, *Gene*, 192, 155-163, 1997; Wolfgang et al., *EMBO J.*, 19, 6408-6418; Mattick, *Annu. Rev. Microbiol.*, 56, 289-314, 2002). Type IV pili are typically 5-7 nm in diameter, several micrometers in length and comprised of a single protein subunit assembled into a helical conformation with ~5 subunits per turn (Bardy et al., *Microbiology*, 149, 295-304, 2003; Wall and Kaiser, *Mol. Microbiol.*, 32, 1-10, 1999). Type IV pilin subunits are usually 145-160 amino acids in length and may be glycosylated or phosphorylated. There are two classes of pilin subunits, type IVa and type IVb, which are distinguished from one another by the average length of the leader peptide and the mature subunit, which N-methylated amino acid occupies the N-terminal position of the mature protein, and the average length of the D-region (for disulfide region). Most of the respiratory pathogens express class IVa pilins, whereas the enteropathogens more typically express class IVb pilins. Type IVa pili are distinguished by the presence of a highly conserved, hydrophobic N-terminal methylated phenylalanine.

Type IV pili serve as a means of rapid translocation over and colonization of new surfaces. Thus type IV pilus expression is important to both adherence and biofilm formation by many bacteria (Mattick, *Annu. Rev. Microbiol.*, 56, 289-314 2002; O'Toole and Kolter, *Mol. Microbiol.*, 30, 295-304, 1998; Klausen et al., *Mol. Microbiol.*, 50, 61-68, 2003; Jesaitis et al., *J. Immunol.*, 171, 4329-4339, 2003), as well as virulence of *Neisseria* species, *Moraxella bovis*, *Vibrio cholerae*, enteropathogenic *Escherichia coli* and *Pseudomonas aeruginosa*, among others (O'Toole and Kolter, supra; Klausen et al., supra; Klausen et al., *Mol. Microbiol.*, 48, 1511-1524, 2003; Strom and Lory, *Annu. Rev. Microbiol.*, 47, 565-596, 1993). A biofilm is a complex organization of bacteria that are anchored to a surface via a bacterially extruded matrix, comprised of exopolysaccharide or other substances. The matrix envelopes the bacteria and protects it from the human immune system. Ehrlich et al., *JAMA*, 287(13), 1710-1715 (2002) describes biofilm formation by *H. influenzae*. It has been postulated that blocking the interaction between type IV pili and the human body can avoid or stop the bacterial infection (Meyer et al., U.S. Pat. No. 6,268,171 issued Jul. 31, 2001).

Type IV pilus expression is a complex and highly regulated bacterial function. In *P. aeruginosa*, the biogenesis and function of type IV pili is controlled by over forty genes (Strom and Lory, supra). To date, only a subset of the vast number of related type IV pilus genes (Tonjum and Koomey, supra; Darzins and Russell, *Gene*, 192, 109-115, 1997) have been found in several members of the HAP (*Haemophilus, Actinobacillus* and *Pasteurella*) family (Stevenson et al., *Vet. Microbiol.*, 92, 121-134, 2003; Doughty et al., *Vet. Microbiol.*, 72, 79-90, 2000; Dougherty and Smith, *Microbiology*, 145, 401-409 1999), but neither expression of type IV pili nor twitching motility has ever been described for any *H. influenzae* isolate. In fact, *H. influenzae* is classically described as a bacterium that does not express these structures (Friedrich et al. *Appl. Environ. Microbiol.*, 69, 3695-3700, 2003; Fussenegger et al., *Gene*, 192, 125-134, 1997), despite the presence of a cryptic gene cluster within the strain Rd genome (Fleischmann et al., *Science*, 269, 496-512, 1995). Strain Rd is a non-encapsulated derivative of an *H. influenzae* serotype d organism (Zwahlen et al., *Infect. Immun.*, 42, 708-715, 1983; Bendler and Goodgal, *J. Microbiol.*, 70, 411-422, 1972; Risberg et al., *Eur. J. Biochem.*, 261, 171-180, 1999). Although strain Rd has some virulence properties, serotype d strains are generally considered to be commensals; they do not frequently cause disease (Daines et al., *J. Med. Microbiol.*, 52, 277-282, 2003). It is therefore important to make the distinction between disease-causing strains of *H. influenzae* and strain Rd.

Fimbriae, which are surface appendages found on nontypable *Haemophilus influenzae*, are produced by 100% of the bacteria recovered from the middle ears and nasopharyngeal region of children with chronic otitis media. A vaccine comprised of fimbrin, a filamentous protein derived from the fimbriae of non-typable *Haemophilus influenzae* was previously developed and is useful in studying, preventing, or reducing the severity of otitis media. However, existing methodologies to isolate fimbrin protein from the bacterial outer membrane are tedious and time-consuming. Similarly, purification of fimbrin expressed by the fimbrin gene in other host vector, is also tedious due to the homology between the fimbrin protein and the outer membrane proteins of the host vector.

The synthetic chimeric vaccine candidate, denoted as LB1 and described in U.S. Pat. No. 5,843,464, has shown tremendous efficacy in multiple pre-clinical vaccine trials in two rodent hosts. This synthetic peptide comprises a B-cell epitope of P5-fimbrin collinearly synthesized with a T-cell promiscuous epitope derived from a fusion protein of the measles vaccine. Whereas LB1 peptide has been shown to be efficacious in pre-clinical trials, there is concern about the ability to test and market a vaccine that contains a T-cell promiscuous epitope for intended use in very young children. Therefore, there is a need to develop vaccine candidate that elicit a specific and controlled immune response to *H. influenzae*.

SUMMARY OF THE INVENTION

The present invention relates to chimeric proteins comprising a portion of the Type IV pilus major subunit protein (PilA) of nontypeable *H. influenzae* (NTHi) and a portion of NTHi OMP P5 protein (also called P5-fimbrin, fimbrin or OMP P5-homologous adhesin). In particular, the invention provides for chimeric proteins comprising PilA modified to present the B-cell epitope of the LB1 peptide. The invention also provides vaccine compositions comprising one or more chimeric proteins of the invention and methods of eliciting an immune response using the chimeric proteins of the invention.

The LB1 peptide is a 40 amino acid synthetic chimeric P5-fimbrin derived peptide (SEQ ID NO: 53) that induces an immunogenic response to NTHi and is advantageous because it does not require tedious purification techniques. The LB1 peptide comprises an N-terminal 19 amino acid peptide that is a B-cell epitope (SEQ ID NO: 4). The B-cell epitope was derived from the predicted surface-exposed loop 3 of an outer membrane protein (fimbrin) of NTHi denoted as OMP P5 (also called P5-fimbrin or OMP P5-homologous adhesin). The LB1 peptide further comprises a short 5-mer linker peptide and a 16-residue T cell promiscuous epitope. The T cell epitope was derived from a fusion protein of the measles virus. The T cell promiscuous epitope induces a very strong T cell response in individuals exposed to this epitope.

The present invention contemplates inserting a portion or fragment of the LB1 peptide into a safer and selective carrier protein that does not reduce the effectiveness of inducing a B-cell response. Preferably, the portion of the LB1 peptide is inserted into a carrier that itself also confers protection against NTHi-induced diseases. One such carrier that may induce protection against NTHi induced diseases is the protein that comprises the NTHi Type IV pilus (twitching pilus)

protein, also known as PilA protein (SEQ ID NO: 2). The PilA protein is encoded by the pilA gene (SEQ ID NO: 1).

The present invention provides for chimeric proteins comprising a portion of the LB1 peptide in order to present the peptide to induce an immunogenic response. The invention contemplates presenting a portion of the LB1 peptide that is 12 to 35 amino acids, more preferably presenting a portion of the LB1 peptide that is 15 to 30 amino acids, and most preferably presenting a portion of the LB1 peptide that is 18 to 19 amino acids and is a subunit of the fimbrin protein. A preferred portion of the LB1 peptide is the N-terminal amino acid sequence RSDYKFYEDANGTRDHKKG (SEQ ID NO: 4).

In another embodiment, the invention provides for chimeric protein wherein the PilA protein is modified to present a 24 amino acid peptide. The 24 amino acid peptide may comprise the B-cell epitope of the LB1 peptide modified as set out in the amino acid sequence of SEQ ID NO: 5 (LVRSDYKFYEDANGTRDHKKGRHT) in which a leucine and valine are added to the N terminus of the B-cell epitope of LB1 and an arginine, histidine and threonine are at the C terminus of the B-cell epitope of LB1. These modifications to the B-cell epitope are contemplated to assist in protein folding and/or antigen presentation. The invention further contemplates any modifications to the B-cell epitope of LB1 that will assist in protein folding and/or antigen presentation.

The amino acid sequence of the surface exposed loop 3 of NTHi OMP P5 can vary between NTHi strains. The invention contemplates chimeric proteins comprising a portion of the PilA protein modified to present the B cell epitope of any variant amino acid sequence of loop 3 of the NTHi OMP P5. In particular, the invention provides for chimeric proteins wherein the PilA protein is modified to present one of the following variant NTHi OMP P5 amino acids sequences: RSDYKLYNKNSSSNSTLKNLGE (SEQ ID NO: 6), RSDYKLYNKNSSTLKDLGE (SEQ ID NO: 7) and RSDYKFYDNKRID (SEQ NO: 8). The variant peptides also may be presented with a leucine and valine added to the N terminus and an arginine, histidine and threonine added to the C terminus or any other modification to assist in protein folding and/or antigen presentation.

The chimeric proteins of the invention comprise the modified PilA amino acids wherein the native PilA amino acids have been substituted with a portion of the LB1 peptide. In addition, the chimeric proteins of the invention comprise a modified PilA amino acid sequence wherein a portion of the LB1 peptide is inserted within and in addition to the native PilA amino acids. The chimeric proteins of the invention have the ability to induce the formation of antibodies directed against two proteins and therefore are more effective and more specific vaccine candidates.

In one embodiment, the chimeric proteins comprise the mature amino acid sequence (residues 13-149) of the NTHi PilA protein (SEQ ID NO: 2) wherein a portion of the LB1 peptide is inserted between the cysteine residues at positions 62 and 72 of SEQ ID NO: 2 and may substitute the native amino acids, such as the chimeric protein having the amino acid sequence of SEQ ID NO: 54. This chimeric protein comprises residues 40-149 of SEQ ID NO: 2 and has the B-cell epitope of LB1 (SEQ ID NO: 5) inserted between residues 62 and 72 of SEQ ID NO: 2. In another embodiment, the portion of the LB1 peptide is inserted between the cysteine residues at positions 131 and 144 of SEQ ID NO: 2 and may substitute the native amino acids such as the protein having the amino acid sequence of SEQ ID NO: 55. This chimeric protein comprises residues 40-149 of SEQ ID NO: 2 and has the B-cell epitope of LB1 (SEQ ID NO: 5) inserted between residues 131 and 144 of SEQ ID NO: 2.

In another embodiment, the chimeric proteins comprise the mature amino acid sequence (residues 13-149) of the NTHi PilA protein (SEQ ID NO: 2) wherein the portion of the LB1 peptide is inserted at the C-terminus of the PilA protein. For example, the chimeric protein of SEQ ID NO: 56 comprises residues 40-149 of SEQ ID NO: 2 and the B-cell epitope of LB1 (SEQ ID NO: 5) is inserted following residue 149 of SEQ ID NO: 2.

In another embodiment, the chimeric proteins comprise the mature amino acid sequence (residues 13-149) of NTHi PilA protein (SEQ ID NO: 2) wherein the portion of the LB1 peptide is inserted at the N-terminus of the PilA protein. For example, the chimeric protein of SEQ ID NO: 57 comprises residues 40-149 of SEQ ID NO: 2 and the B-cell epitope of LB1 (SEQ ID NO: 5) is inserted before residue 40 of SEQ ID NO: 2.

In a further embodiment, the invention provides for chimeric proteins comprising a portion of the NTHi PilA protein and one or more of the LB1 peptides described herein. The chimeric proteins of the invention include those which present the same LB1 peptide more than once within a portion of the NTHi PilA protein and those which present two or more different LB1 peptides within a portion of the NTHi PilA protein.

The invention further provides for chimeric proteins comprising a portion of the NTHi PilA protein and any antigenic protein that will elicit an immune response.

The NTHi Type IV Pilus (PilA) Polynucleotides and Polypeptides of the Invention

The chimeric proteins of the invention may comprise the full length or a portion of the major subunit of the NTHi Type IV Pilus which is encoded by the gene pilA. The PilA protein of the NTHi isolate 86-028NP is encoded by the nucleic acid sequence set out as SEQ ID NO: 2, which is described in U.S. patent application Ser. No. 11/019,005, incorporated by reference herein in its entirety. Also provided are polynucleotides encoding PilA polypeptides from NTHi clinical isolates 1728MEE, 1729MEE, 3224A, 10548MEE, 1060MEE, 1885MEE, 1714MEE, 1236MEE, 1128MEE and 214NP. The amino acid sequences of these PilA polypeptides are set out in SEQ ID NOS: 34, 36, 38, 40, 42, 44, 46, 48, 50 and 52 respectively. The possibility of alternative codon usage is specifically contemplated in polynucleotides encoding the polypeptides. In one embodiment, the polypeptides are respectively encoded by the nucleotide sequences set out in SEQ ID NOS: 33, 35, 37, 39, 41, 43, 45, 47, 49 and 51.

The invention provides for polynucleotides that hybridize under stringent conditions to (a) the complement of the nucleotide sequences set out in SEQ ID NOS: 1, 33, 35, 37, 39, 41, 43, 45, 47, 49 and 51; (b) a polynucleotide which is an allelic variant of any polynucleotides recited above; (c) a polynucleotide which encodes a species homolog of any of the proteins recited above; or (d) a polynucleotide that encodes a polypeptide comprising a specific domain or truncation of the polypeptides of the present invention. PilA polynucleotides from other non-typeable *H. influenzae* strains and from *H. influenzae* strains a, b, c, e and f are specifically contemplated. These polynucleotides can be identified and isolated by techniques standard in the art such as hybridization and polymerase chain reaction using part or all of the polynucleotides of SEQ ID NOS: 1, 33, 35, 37, 39, 41, 43, 45, 47, 49 and 51 as probes or primers, respectively.

The polynucleotides of the invention also include nucleotide sequences that are substantially equivalent to the polynucleotides recited above. Polynucleotides according to the invention can have, e.g., at least 65%, at least 70%, at least 75%, at least 80%, 81%, 82%, 83%, 84%, 85%, 86%, 87%, 88%, or 89%, more typically at least 90%, 91%, 92%, 93%, or 94% and even more typically at least 95%, 96%, 97%, 98% or 99% sequence identity to the NTHi polynucleotides recited above.

Included within the scope of the nucleic acid sequences of the invention are nucleic acid sequence fragments that hybridize under stringent conditions to the NTHi nucleotide sequences of SEQ ID NOS: 1, 33, 35, 37, 39, 41, 43, 45, 47, 49 and 51, or complements thereof, which fragment is greater than about 5 nucleotides, preferably 7 nucleotides, more preferably greater than 9 nucleotides and most preferably greater than 17 nucleotides. Fragments of, e.g., 15, 17, or 20 nucleotides or more that are selective for (i.e., specifically hybridize to any one of the PilA polynucleotides of the invention) are contemplated. These nucleic acid sequence fragments capable of specifically hybridizing to an NTHi PilA polynucleotide of the invention can be used as probes to detect NTHi PilA polynucleotides of the invention and/or can differentiate NTHi PilA polynucleotides of the invention from other bacterial genes, and are preferably based on unique nucleotide sequences.

The term "stringent" is used herein to refer to conditions that are commonly understood in the art as stringent. Hybridization stringency is principally determined by temperature, ionic strength, and the concentration of denaturing agents such as formamide. Examples of stringent conditions for hybridization and washing are 0.015 M sodium chloride, 0.0015 M sodium citrate at 65-68° C. or 0.015 M sodium chloride, 0.0015M sodium citrate, and 50% formamide at 42° C. See Sambrook et al., *Molecular Cloning: A Laboratory Manual*, 2$^{nd}$ Ed., Cold Spring Harbor Laboratory, (Cold Spring Harbor, N.Y. 1989).

More stringent conditions (such as higher temperature, lower ionic strength, higher formamide, or other denaturing agent) may also be used, however, the rate of hybridization will be affected. In instances wherein hybridization of deoxyoligonucleotides is concerned, additional exemplary stringent hybridization conditions include washing in 6×SSC 0.05% sodium pyrophosphate at 37° C. (for 14-base oligos), 48° C. (for 17-base oligos), 55° C. (for 20-base oligos), and 60° C. (for 23-base oligos).

Other agents may be included in the hybridization and washing buffers for the purpose of reducing non-specific and/or background hybridization. Examples are 0.1% bovine serum albumin, 0.1% polyvinyl-pyrrolidone, 0.1% sodium pyrophosphate, 0.1% sodium dodecylsulfate, NaDodSO$_4$, (SDS), ficoll, Denhardt's solution, sonicated salmon sperm DNA (or other non-complementary DNA), and dextran sulfate, although other suitable agents can also be used. The concentration and types of these additives can be changed without substantially affecting the stringency of the hybridization conditions. Hybridization experiments are usually carried out at pH 6.8-7.4, however, at typical ionic strength conditions, the rate of hybridization is nearly independent of pH. See Anderson et al., *Nucleic Acid Hybridisation: A Practical Approach*, Ch. 4, IRL Press Limited (Oxford, England). Hybridization conditions can be adjusted by one skilled in the art in order to accommodate these variables and allow DNAs of different sequence relatedness to form hybrids.

As noted above, polynucleotides contemplated by the present invention are not limited to the specific PilA polynucleotides of SEQ ID NOS: 1, 33, 35, 37, 39, 41, 43, 45, 47, 49 and 51, but also include, for example, allelic and species variations thereof. Allelic and species variations can be routinely determined by comparing the sequence provided in SEQ ID NOS: 1, 33, 35, 37, 39, 41, 43, 45, 47, 49 and 51, preferably the open reading frames therein, a representative fragment thereof, or a nucleotide sequence at least 90% identical, preferably 95% identical, to the open reading frames within SEQ ID NOS: 1, 33, 35, 37, 39, 41, 43, 45, 47, 49 and 51 with a sequence from another isolate of the same species or another species. Preferred computer program methods to determine identity and similarity between two sequences include, but are not limited to, the GCG program package, including GAP (Devereux et al., *Nucl. Acid. Res.*, 12: 387, 1984; Genetics Computer Group, University of Wisconsin, Madison, Wis.), BLASTP, BLASTN, and FASTA (Altschul et al., *J. Mol. Biol.*, 215: 403-410, 1990). The BLASTX program is publicly available from the National Center for Biotechnology Information (NCBI) and other sources (*BLAST Manual*, Altschul et al. NCB/NLM/NIH Bethesda, Md. 20894; Altschul et al., supra). The well known Smith-Waterman algorithm may also be used to determine identity.

Polynucleotides of the invention may be isolated from natural sources or may be synthesized by standard chemical techniques, e.g., the phosphotriester method described in Matteucci et al., *J Am Chem. Soc.*, 103: 3185 (1981).

The invention provides for chimeric proteins comprising a portion of NTHi PilA protein. In one embodiment polypeptides comprise the NTHi 86-028NP amino acid sequences respectively set out in SEQ ID NO: 2. Polypeptides of the invention also include PilA polypeptides set out in SEQ ID NOS: 34, 36, 38, 40, 42, 44, 46, 48, 50 and 52. In additional embodiments, the PilA polypeptides of the invention are those of other non-typeable *H. influenzae* strains and from *H. influenzae* strains a, b, c, e and f.

Polypeptides of the invention specifically include peptide fragments (i.e., peptides) or fragments of the PilA polypeptide that retain one or more biological or immunogenic properties of a full length polypeptide of the invention. In one embodiment, PilA peptide fragments provided by the invention are designated TfpQ2, TfpQ3, TfpQ4 and OLP3 and respectively comprise amino acids 35 through 68 of SEQ ID NO: 2, amino acids 69 through 102 of SEQ ID NO: 2, amino acids 103 through 137 of SEQ ID NO: 2, and amino acids 21 through 35 of SEQ ID NO: 2. Another PilA peptide fragment provided by the invention comprises amino acids 40 through 149 of SEQ ID NO: 2.

The invention also provides for chimeric proteins comprising a portion of a PilA polypeptide with one or more conservative amino acid substitutions that do not affect the biological and/or immunogenic activity of the PilA polypeptide. Alternatively, the PilA polypeptides of the invention are contemplated to have conservative amino acids substitutions which may or may not alter biological activity. The term "conservative amino acid substitution" refers to a substitution of a native amino acid residue with a normative residue, including naturally occurring and nonnaturally occurring amino acids, such that there is little or no effect on the polarity or charge of the amino acid residue at that position. For example, a conservative substitution results from the replacement of a non-polar residue in a polypeptide with any other non-polar residue. Further, any native residue in the polypeptide may also be substituted with alanine, according to the methods of "alanine scanning mutagenesis". Naturally occurring amino acids are characterized based on their side chains as follows: basic: arginine, lysine, histidine; acidic: glutamic acid, aspartic acid; uncharged polar: glutamine, asparagine, serine, threonine, tyrosine; and non-polar: phenylalanine, tryptophan, cysteine, glycine, alanine, valine, proline, methionine, leucine, norleucine, isoleucine General rules for amino acid substitutions are set forth in Table 1 below.

TABLE 1

Amino Acid Substitutions

| Original Residues | Exemplary Substitutions | Preferred Substitutions |
|---|---|---|
| Ala | Val, Leu, Ile | Val |
| Arg | Lys, Gln, Asn | Lys |
| Asn | Gln | Gln |
| Asp | Glu | Glu |
| Cys | Ser, Ala | Ser |
| Gln | Asn | Asn |
| Glu | Asp | Asn |
| Gly | Pro, Ala | Ala |
| His | Asn, Gln, Lys, Arg | Arg |
| Ile | Leu, Val, Met, Ala, Phe, | Leu |
| Leu | Norleucine, Ile, Val, Met, | Leu |
| Lys | Arg, 1,4 Diaminobutyric | Arg |
| Met | Leu, Phe, Ile | Leu |
| Phe | Leu, Val, Ile, Ala, Tyr | Arg |
| Pro | Ala | Gly |
| Ser | Thr, Ala, Cys | Thr |
| Thr | Ser | Ser |
| Trp | Tyr, Phe | Tyr |
| Tyr | Trp, Phe, Thr, Ser | Phe |
| Val | Ile, Met, Leu, Phe, Ala, | Leu |

The invention also provides for chimeric proteins comprising a portion of a variants of the NTHi PilA polypeptides of the present invention (e.g., a polypeptide exhibiting at least about 65%, at least about 70%, at least about 75%, at least about 80%, at least about 85%, 86%, 87%, 88%, 89%, at least about 90%, 91%, 92%, 93%, 94%, typically at least about 95%, 96%, 97%, more typically at least about 98%, or most typically at least about 99% amino acid identity to a polypeptide of SEQ ID NOS: 2, 34, 36, 38, 40, 42, 44, 46, 48, 50 and 52) that retain biological and/or immunogenic activity.

The invention contemplates that PilA polynucleotides of the invention may be inserted in a vector for amplification or expression. For expression, the polynucleotides are operatively linked to appropriate expression control sequences such as promoter and polyadenylation signal sequences. Further provided are host cells comprising polynucleotides of the invention. Exemplary prokaryotic host cells include bacteria such as *E. coli*, *Bacillus*, *Streptomyces*, *Pseudomonas*, *Salmonella* and *Serratia*. Methods of producing polypeptides of the invention by growing the host cells and isolating polypeptide from the host cells or growth medium are specifically contemplated. Alternatively, polypeptides of the invention can be prepared by chemical synthesis using standard means. Particularly convenient are solid phase techniques (see, e.g., Erikson et al., *The Proteins* (1976) v. 2, Academic Press, New York, p. 255). Automated solid phase synthesizers are commercially available. In addition, modifications in the sequence are easily made by substitution, addition or omission of appropriate residues. For example, a cysteine residue may be added at the carboxy terminus to provide a sulfhydryl group for convenient linkage to a carrier protein, or spacer elements, such as an additional glycine residue, may be incorporated into the sequence between the linking amino acid at the C-terminus and the remainder of the peptide.

The term "isolated" refers to a substance removed from, and essentially free of, the other components of the environment in which it naturally exists. For example, a polypeptide is separated from other cellular proteins or a DNA is separated from other DNA flanking it in a genome in which it naturally occurs.

Recombinant PilA protein (rPilA) may be generated to serve as a more readily renewable product. To do this, the published protocol of Keizer et al. (*J. Biol. Chem.*, 276: 24186-14193, 2001), who studied a pilin which also had four Cys residues as it will be critical that rPilA similarly be properly folded so as to possess functional qualities of the native pilin subunit, is utilized. Briefly, a truncated pilin is engineered wherein the first 28 residues are removed from the N-terminus to prevent aggregation, and this truncated pilin will be further engineered to be transported to the periplasm by means of the incorporation of an OmpA leader sequence in the construct. Using this strategy Keizer et al. generated a recombinant soluble monomeric *P. aeruginosa* pilin protein that was able to bind to its receptor (asialo GM1) in in vitro assays and decrease morbidity and mortality in mice when the peptide was delivered 15 minutes prior to heterologous challenge. This soluble, monomeric, truncated form of NTHi PilA will be useful in the studies described herein.

The invention also provides for synthetic chimeric proteins. The chimeric proteins may be synthesize, purified and sequenced using standard techniques. For example, the chimeric proteins may be assembled semi-manually by stepwise Fmoc-tert-butyl solid-phase synthesis and purified by HPLC. The composition and amino acid sequence of recombinant and synthetic chimeric proteins may be confirmed by amino acid analysis and/or mass spectral analysis.

Antibodies

The invention provides antibodies which bind to antigenic epitopes of the chimeric proteins of the invention. The antibodies may be polyclonal antibodies, monoclonal antibodies, antibody fragments which retain their ability to bind their unique epitope (e.g., Fv, Fab and F(ab)2 fragments), single chain antibodies and human or humanized antibodies. Antibodies may be generated by techniques standard in the art using chimeric protein(s) of the invention or host cells expressing chimeric protein(s) of the invention as antigens.

The present invention provides for antibodies specific for the chimeric proteins of the present invention and fragments thereof, which exhibit the ability to kill both *H. influenzae* bacteria and to protect humans from infection. The present invention also provides for antibodies specific for the chimeric proteins of the invention which reduce the virulence, inhibit adherence, inhibit biofilm formation, inhibit twitching motility, inhibit cell division, and/or inhibit penetration into the epithelium of *H. influenzae* bacteria and/or enhance phagocytosis of the *H. influenzae* bacteria.

In vitro complement mediated bactericidal assay systems (Musher et al., *Infect. Immun.* 39: 297-304, 1983; Anderson et al., *J. Clin. Invest.* 51: 31-38, 1972) may be used to measure the bactericidal activity of anti-chimeric proteins antibodies.

It is also possible to confer short-term protection to a host by passive immunotherapy via the administration of pre-formed antibody against a chimeric protein of the invention. Thus, antibodies of the invention may be used in passive immunotherapy. Human immunoglobulin is preferred in human medicine because a heterologous immunoglobulin may provoke an immune response to its foreign immunogenic components. Such passive immunization could be used on an emergency basis for immediate protection of unimmunized individuals subject to special risks.

In another embodiment, antibodies of the invention may be used in the production of anti-idiotypic antibody, which in turn can be used as an antigen to stimulate an immune response against the chimeric protein epitopes or *H. influenzae* epitopes.

Methods for Eliciting an Immune Response and Compositions Therefor

The invention contemplates methods of eliciting in an individual an immune response to *H. influenzae* in an individual. In certain embodiments, the methods elicit an immune response to the chimeric proteins of the invention. These methods elicit one or more immune responses, including but not limited to, immune responses which inhibit bacterial replication, immune responses which block *H. influenzae* adherence to cells, immune responses which prevent *H. influenzae* twitching, immune responses that kill *H. influenzae* bacteria and immune responses which prevent biofilm formation. In one embodiment, the methods comprise a step of administering an immunogenic dose of a composition comprising one or more chimeric proteins of the invention. In another embodiment, the methods comprise administering an immunogenic dose of a composition comprising a cell expressing one or more chimeric proteins of the invention. In yet another embodiment, the methods comprise administering an immunogenic dose of a composition comprising one or more polynucleotides encoding one or more chimeric proteins of the invention. The polynucleotide may be a naked polynucleotide not associated with any other nucleic acid or may be in a vector such as a plasmid or viral vector (e.g., adeno-associated virus vector or adenovirus vector). The methods may be used in combination in a single individual. The methods may be used prior or subsequent to *H. influenzae* infection of an individual. The methods and compositions of the invention may be used to treat or prevent any pathological condition involving *H. influenzae* (typeable and nontypeable strains) such as OM, pneumonia, sinusitis, septicemia, endocarditis, epiglottitis, septic arthritis, meningitis, postpartum and neonatal infections, postpartum and neonatal sepsis, acute and chromic salpingitis, epiglottis, pericardis, cellulitis, osteomyelitis, endocarditis, cholecystitis, intraabdominal infections, urinary tract infection, mastoiditis, aortic graft infection, conjunctivitis, Brazilian purpuric fever, occult bacteremia, chronic obstructive pulmonary disease and exacerbation of underlying lung diseases such as chronic bronchitis, bronchietasis and cystic fibrosis.

In one embodiment of methods of the invention, a composition of the invention is administered as a priming dose followed by one or more booster doses. Co-administration of proteins or polypeptides that beneficially enhance the immune response such as cytokines (e.g., IL-2, IL-12, GM-CSF), cytokine-inducing molecules (e.g. Leaf) or co-stimulatory molecules is also contemplated.

An "immunogenic dose" of a composition of the invention is one that generates, after administration, a detectable humoral (antibody) and/or cellular (T cell) immune response in comparison to the immune response detectable before administration or in comparison to a standard immune response before administration. The invention contemplates that the immune response resulting from the methods may be protective and/or therapeutic. In a preferred embodiment, the antibody and/or T cell immune response protects the individual from *H. influenzae* infection, particularly infection of the middle ear and/or the nasopharynx or lower airway. In this use, the precise dose depends on the patient's state of health and weight, the mode of administration, the nature of the formulation, etc., but generally ranges from about 1.0 μg to about 5000 μg per 70 kilogram patient, more commonly from about 10 to about 500 μg per 70 kg of body weight.

Humoral immune response may be measured by many well known methods, such as Single Radial Immunodiffussion Assay (SRID), Enzyme Immunoassay (ETA) and Hemagglutination Inhibition Assay (HAI). In particular, SRID utilizes a layer of a gel, such as agarose, containing the immunogen being tested. A well is cut in the gel and the serum being tested is placed in the well. Diffusion of the antibody out into the gel leads to the formation of a precipitation ring whose area is proportional to the concentration of the antibody in the serum being tested. ETA, also known as ELISA (Enzyme Linked Immunoassay), is used to determine total antibodies in the sample. The immunogen is adsorbed to the surface of a microtiter plate. The test serum is exposed to the plate followed by an enzyme linked immunoglobulin, such as IgG. The enzyme activity adherent to the plate is quantified by any convenient means such as spectrophotometry and is proportional to the concentration of antibody directed against the immunogen present in the test sample. HAI utilizes the capability of an immunogen such as viral proteins to agglutinate chicken red blood cells (or the like). The assay detects neutralizing antibodies, i.e., those antibodies able to inhibit hemagglutination. Dilutions of the test serum are incubated with a standard concentration of immunogen, followed by the addition of the red blood cells. The presence of neutralizing antibodies will inhibit the agglutination of the red blood cells by the immunogen. Tests to measure cellular immune response include determination of delayed-type hypersensitivity or measuring the proliferative response of lymphocytes to target immunogen.

The invention correspondingly provides compositions suitable for eliciting an immune response to chimeric proteins of the invention. As noted above, the compositions comprise one or more chimeric proteins, cells expressing one or more chimeric proteins, or one or more polynucleotides encoding one or more chimeric proteins. The compositions may also comprise other ingredients such as carriers and adjuvants.

In compositions of the invention, a chimeric protein may be fused to another protein when produced by recombinant methods. In one embodiment, the other protein may not, by itself, elicit antibodies, but it stabilizes the first protein and forms a fusion protein retaining immunogenic activity. In another embodiment, the fusion protein comprises another protein that is immunogenic, such as Glutathione-S-transferase (GST) or beta-galactosidase, relatively large co-proteins which solubilize the fusion protein and facilitate production and purification thereof. The other protein may act as an adjuvant in the sense of providing a generalized stimulation of the immune system. The other protein may be fused to either the amino or carboxy terminus of the chimeric proteins of the invention.

In other compositions of the invention, chimeric proteins may be otherwise linked to carrier substances. Any method of creating such linkages known in the art may be used. Linkages can be formed with hetero-bifunctional agents that generate a disulfide link at one functional group end and a peptide link at the other, such as a disulfide amide forming agent, e.g., N-succidimidyl-3-(2-pyridyldithio) proprionate (SPDP) (See, e.g., Jansen et al., *Immun. Rev.* 62:185, 1982) and bifunctional coupling agents that form a thioether rather than a disulfide linkage such as reactive esters of 6-maleimidocaproic acid, 2-bromoacetic acid, 2-iodoacetic acid, 4-(N-maleimido-methyl)cyclohexane-1-carboxylic acid and the like, and coupling agent which activate carboxyl groups by combining them with succinimide or 1-hydroxy-2-nitro-4-sulfonic acid, for sodium salt such as succinimidyl 4-(N-maleimido-methyl)cyclohexane-1-carboxylate (SMCC).

The chimeric proteins may be formulated as neutral or salt forms. Pharmaceutically acceptable salts, include the acid addition salts (formed with the free amino groups of the peptide) and which are fainted with inorganic acids such as, e.g., hydrochloric or phosphoric acids, or such organic acids as acetic, oxalic, tartaric, mandelic. Salts formed with the free carboxyl groups may also be derived from inorganic bases such as, e.g., sodium, potassium, ammonium, calcium, or ferric hydroxides, and such organic bases as isopropylamine, trimethylamine, 2-ethylamino ethanol, histidine, and procaine.

Compositions of the invention may further comprise adjuvants. Known adjuvants include, for example, emulsions such as Freund's Adjuvants and other oil emulsions, *Bordetella pertussis*, MF59, purified saponin from *Quillaja saponaria* (QS21), aluminum salts such as hydroxide, phosphate and alum, calcium phosphate, (and other metal salts), gels such as aluminum hydroxide salts, mycobacterial products including muramyl dipeptides, solid materials, particles such as liposomes and virosomes. Examples of natural and bacterial products known to be used as adjuvants include monophosphoryl lipid A (MPL), RC-529 (synthetic MPL-like acylated monosaccharide), OM-174 which is a lipid A derivative from *E. coli*, holotoxins such as cholera toxin (CT) or one of its derivatives, pertussis toxin (PT) and heat-labile toxin (LT) of *E. coli* or one of its derivatives, and CpG oligonucleotides. Adjuvant activity can be affected by a number of factors, such as carrier effect, depot formation, altered lymphocyte recirculation, stimulation of T-lymphocytes, direct stimulation of B-lymphocytes and stimulation of macrophages.

Compositions of the invention are typically formulated as injectables, either as liquid solutions or suspensions; solid forms suitable for solution in, or suspension in, liquid prior to injection may also be prepared. The preparation may also be emulsified. The active immunogenic ingredient is often mixed with excipients, which are pharmaceutically acceptable and compatible with the active ingredient. Suitable excipients are, e.g., water, saline, dextrose, glycerol, ethanol, or the like and combinations thereof. In addition, if desired, the vaccine may contain minor amounts of auxiliary substances such as wetting or emulsifying agents, pH buffering agents, or adjuvants, which enhance the effectiveness of the vaccine. The vaccines are conventionally administered parenterally, by injection, for example, either subcutaneously or intramuscularly.

Additional formulations which are suitable for other modes of administration include suppositories and, in some cases, oral formulations. For suppositories, traditional binders and carriers may include, for example, polyalkalene glycols or triglycerides; such suppositories may be formed from mixtures containing the active ingredient in the range of 0.5% to 10%, preferably 1-2%. Oral formulations include such normally employed excipients as, for example, pharmaceutical grades of mannitol, lactose, starch, magnesium stearate, sodium saccharine, cellulose, magnesium carbonate and the like. These compositions take the form of solutions, suspensions, tablets, pills, capsules, sustained release formulations or powders and contain 10%-95% of active ingredient, preferably 25-70%.

Compositions may also be administered through transdermal routes utilizing jet injectors, microneedles, electroporation, sonoporation, microencapsulation, polymers or liposomes, transmucosal routes and intranasal routes using nebulizers, aerosols and nasal sprays. Microencapsulation using natural or synthetic polymers such as starch, alginate and chitosan, D-poly L-lactate (PLA), D-poly DL-lacticoglycolic microspheres, polycaprolactones, polyorthoesters, polyanhydrides and polyphosphazenes polyphosphatazanes are useful for both transdermal and transmucosal administration. Polymeric complexes comprising synthetic poly-ornithate, poly-lysine and poly-arginine or amphipathic peptides are useful for transdermal delivery systems. In addition, due to their amphipathic nature, liposomes are contemplated for transdermal, transmucosal and intranasal vaccine delivery systems. Common lipids used for vaccine delivery include N-(1)2,3-(dioleyl-dihydroxypropyl)-N,N,N-trimethylammonium-methyl sulfate (DOTAP), dioleyloxy-propyl trimethylammonium chloride DOTMA, dimystyloxypropyl-3-dimethyl-hydroxyethyl ammonium (DMRIE), dimethyldioctadecyl ammonium bromide (DDAB) and 9N(N',N-dimethylaminoethane)carbamoyl) cholesterol (DC-Chol). The combination of helper lipids and liposomes will enhance up-take of the liposomes through the skin. These helper lipids include dioleoyl phosphatidylethanolamine (DOPE), dilauroylphosphatidylethanolamine (DLPE), dimyristoyl phosphatidylethanolamine (DMPE), dipalmitoylphosphatidylethanolamine (DPPE). In addition, triterpenoid glycosides or saponins derived from the Chilean soap tree bark (*Quillaja saponaria*) and chitosan (deacetylated chitan) have been contemplated as useful adjuvants for intranasal and transmucosal vaccine delivery.

Formulations may be presented in unit-dose or multi-dose containers, for example, sealed ampules and vials and may be stored in a freeze-dried condition requiring only the addition of the sterile liquid carrier immediately prior to use.

Methods of Inhibiting *H. influenzae*

Alternatively, the invention includes methods of inhibiting *H. influenzae* type IV pili function in an individual. The methods comprise administering to the individual, for example, one or more antibodies of the invention and/or one or more chimeric proteins of the invention; in an amount that inhibits function of the pili. In vitro assays may be used to demonstrate the ability to inhibit pili function. Embodiments of these methods include, for example, methods using inhibitors of adherence mediated via type IV pili, inhibitors that disrupt existing biofilms mediated by type IV pili, and inhibitors of twitching.

Inhibition is contemplated for any pathological condition involving *H. influenzae*, for example, OM, pneumonia, sinusitis, septicemia, endocarditis, epiglottitis, septic arthritis, meningitis, postpartum and neonatal infections, postpartum and neonatal sepsis, acute and chromic salpingitis, epiglottis, pericardis, cellulitis, osteomyelitis, endocarditis, cholecystitis, intraabdominal infections, urinary tract infection, mastoiditis, aortic graft infection, conjunctitivitis, Brazilian purpuric fever, occult bacteremia, chronic obstructive pulmonary disease and exacerbation of underlying lung diseases such as chronic bronchitis, bronchietasis and cystic fibrosis.

Compositions comprising inhibitors of *H. influenzae* type IV pili function are provided. The compositions may consist of one of the foregoing active ingredients alone, may comprise combinations of the foregoing active ingredients or may comprise additional active ingredients used to treat bacterial infections. As discussed above, the compositions may comprise one or more additional ingredients such as pharmaceutically effective carriers. Also as discussed above, dosage and frequency of the administration of the compositions are determined by standard techniques and depend, for example, on the weight and age of the individual, the route of administration, and the severity of symptoms. Administration of the pharmaceutical compositions may be by routes standard in the art, for example, parenteral, intravenous, oral, buccal, nasal, pulmonary, rectal, intranasal, or vaginal.

Animal Model

Methods of the invention may be demonstrated in a chinchilla model widely accepted as an experimental model for OM. In particular, a chinchilla model of NTHi-induced OM has been well characterized (Bakaletz et al., *Infect. Dis.*, 168: 865-872, 1993; Bakaletz and Holmes, *Clin. Diagn. Lab. Immunol.*, 4: 223-225, 1997; Suzuki and Bakaletz, *Infect. Immun.*, 62: 1710-1718, 1994; Mason et al., *Infect. Immun.*, 71:3454-3462, 2003), and has been used to determine the protective efficacy of several NTHi outer membrane proteins, combinations of outer membrane proteins, chimeric synthetic peptide vaccine components, and adjuvant formulations against OM (Bakaletz et al., *Vaccine*, 15: 955-961, 1997; Bakaletz et al., *Infect. Immun.*, 67: 2746-2762, 1999; Kennedy et al., *Infect. Immun.*, 68: 2756-2765, 2000; Kyd et al., *Infect. Immun.*, 66:2272-2278, 2003; Novotny and Bakaletz, *J. Immunol.*, 171, 1978-1983, 2003).

In the model, adenovirus predisposes chinchillas to *H. influenzae*-induced OM media, which allowed for the establishment of relevant cell, tissue and organ culture systems for the biological assessment of NTHi (Bakaletz et al., *J. Infect. Dis.*, 168: 865-72, 1993; Suzuki et al., *Infect. Immunity* 62: 1710-8, 1994). Adenovirus infection alone has been used to assess the transudation of induced serum antibodies into the tympanum (Bakaletz et al., *Clin. Diagnostic Lab Immunol.*, 4(2): 223-5, 1997) and has been used as a co-pathogen with NTHi, to determine the protective efficacy of several active and passive immunization regimens targeting various NTHi outer membrane proteins, combinations of OMPs, chimeric synthetic peptide vaccine components, and adjuvant formulations as vaccinogens against otitis media (Bakaletz et al., *Infect Immunity*, 67(6): 2746-62, 1999; Kennedy et al., *Infect. Immun.*, 68(5): 2756-65, 2000; Novotny et al., *Infect Immunity* 68(4): 2119-28, 2000; Poolman et al., *Vaccine* 19 (Suppl. 1): S108-15, 2000).

BRIEF DESCRIPTION OF DRAWING

FIG. 1 provides the timeline of the immunization regimen, viral inoculation, bacterial challenge, and OM disease assessment period for the efficacy experiments described in Example 5.

DETAILED DESCRIPTION OF THE INVENTION

The following examples illustrate the invention wherein Example 1 describes recombinant production of chimeric proteins of the invention, Example 2 describes assays to test the immunogenicity of the chimeric proteins of the invention, Example 3 describes assays for evaluating passive immunization, Example 4 describes assays for evaluating active immunization and Example 5 describes the evaluation of a chimeric protein of the invention.

EXAMPLE 1

Synthesis of Chimeric Proteins

The chimeric proteins of the invention were produced using standard recombinant methods. Initially, a gene-synthesis company, (Blue Heron Biotechnology Inc.) was contracted to make the initial plasmid based on the chimeric protein amino acid sequences described herein that were optimized for *E. coli* preferred codon usage. Briefly, the native NTHi pilin protein sequence was modified by truncating the N-terminus (residues 1-39 of SEQ ID NO: 2) and adding a HIS-tag sequence and a thrombin cleavage site as set out in SEQ ID NO: 3. The HIS-tag was preceded by a sequence (MUSS) to assist in expression. The thrombin cleavage site allowed for release of the HIS-tag. These plasmids were then cloned into the *E. coli* expression vector pET-15b vector (Novagen). The plasmid were then transformed into *E. coli* strain "Origami(DE3)" (available from Novagen) as the host for expression of soluble His-tagged chimeric proteins. Another *E. coli* host cell expression stain that may be used is Origami B(DE3) (Novagen).

The His-tagged variants of the chimeric proteins will be recovered by nickel column chromatography, then used for initial studies to determine if they are reactive with antisera directed against any of the following: native OMP P5-fimbrin, LB1 (full length 40 amino acid peptide), LB1(1) (a synthetic peptide representing just the 19 amino acid B-cell epitope of LB1), recombinant PilA protein or native PilA protein. Once the His-tag is removed by thrombin site cleavage, the recombinant chimeric proteins will be used as immunogens to determine their immunogenicity and protective capability.

Exemplary chimeric proteins of the invention have the sequences as set out in Table 2 below. The chimeric proteins having the amino acid sequences of SEQ ID NOS: 10, 12 and 14 have been expressed by *E. coli* as described above.

TABLE 2

| SEQ ID NO: | Chimeric Protein Amino Acid Sequence |
|---|---|
| 9 | MGSSHHHHHSSGLVPRGSHMTKKAAVSELLQASAPYKADVEL CRSDYKFYEDANGTRDHKKGCTGGKNGIAADITTAKGYVKSV TTSNGAITVKGDGTLANMEYILQATGNAATGVTWTTCKGTDA SLFPANFCGSVTQ |
| 10 | MGSSHHHHHSSGLVPRGSHMTKKAAVSELLQASAPYKADVEL CLVRSDYKFYEDANGTRDHKKGHTCTGGKNGIAADITTAKGY VKSVTTSNGAITVKGDGTLANMEYILQATGNAATGVTWTTCK GTDASLFPANFCGSVTQ |
| 11 | MGSSHHHHHSSGLVPRGSHMTKKAAVSELLQASAPYKADVEL CVTSTNETTNCTGGKNGIAADITTAKGYVKSVTTSNGAITVKG DGTLANMEYILQATGNAATGVTWTTCRSDYKFYEDANGTRD HKKGCGSVTQ |
| 12 | MGSSHHHHHSSGLVPRGSHMTKKAAVSELLQASAPYKADVEL CVTSTNETTNCTGGKNGIAADITTAKGYVKSVTTSNGAITVKG DGTLANMEYILQATGNAATGVTWTTCLVRSDYKFYEDANGTR DHKKGRHTCGSVTQ |
| 13 | MGSSHHHHHSSGLVPRGSHMTKKAAVSELLQASAPYKADVEL CVTSTNETTNCTGGKNGIAADITTAKGYVKSVTTSNGAITVKG DGTLANMEYILQATGNAATGVTWTTCKGTDASLFPANFCGSV TQRSDYKFYEDANGTRDHKKG |
| 14 | MGSSHHHHHSSGLVPRGSHMTKKAAVSELLQASAPYKADVEL CVTSTNETTNCTGGKNGIAADITTAKGYVKSVTTSNGAITVKG DGTLANMEYILQATGNAATGVTWTTCKGTDASLFPANFCGSV TQLVRSDYKFYEDANGTRDHKKGRHT |
| 15 | MGSSHHHHHSSGLVPRGSHMTKKAAVSELLQASAPYKADVEL CRSDYKLYNKNSSSNSTLKNLGECTGGKNGIAADITTAKGYVK SVTTSNGAITVKGDGTLANMEYILQATGNAATGVTWTTCKGT DASLFPANFCGSVTQ |
| 16 | MGSSHHHHHSSGLVPRGSHMTKKAAVSELLQASAPYKADVEL CLVRSDYKLYNKNSSSNSTLKNLGERHTCTGGKNGIAADYITA KGYVKSVTTSNGAITVKGDGTLANMEYILQATGNAATGVTWT TCKGTDASLFPANFCGSVTQ |
| 17 | MGSSHHHHHSSGLVPRGSHMTKKAAVSELLQASAPYKADVEL CVTSTNETTNCTGGKNGIAADITTAKGYVKSVTTSNGAITVKG DGTLANMEYILQATGNAATGVTWTTCRSDYKLYNKNSSSNST LKNLGECGSVTQ |
| 18 | MGSSHHHHHSSGLVPRGSHMTKKAAVSELLQASAPYKADVEL CVTSTNETTNCTGGKNGIAADITTAKGYVKSVTTSNGAITVKG DGTLANMEYILQATGNAATGVTWTTCLVRSDYKLYNKNSSSN STLKNLGERHTCGSVTQ |
| 19 | MGSSHHHHHSSGLVPRGSHMTKKAAVSELLQASAPYKADVEL CVTSTNETTNCTGGKNGIAADITTAKGYVKSVTTSNGAITVKG DGTLANMEYILQATGNAATGVTWTTCKGTDASLFPANFCGSV TQRSDYKLYNKNSSSNSTLKNLGE |

TABLE 2-continued

| SEQ ID NO: | Chimeric Protein Amino Acid Sequence |
|---|---|
| 20 | MGSSHHHHHSSGLVPRGSHMTKKAAVSELLQASAPYKADVEL CVTSTNTTNCTGGKNGIAADITTAKGYVKSVTTSNGAITVKG DGTLANMEYILQATGNAATGVTWTTCKGTDASLFPANFCGSV TQLVRSDYKLYNKNSSSNSTLKNLGERHT |
| 21 | MGSSHHHHHSSGLVPRGSHMTKKAAVSELLQASAPYKADVEL CRSDYKLYNKNSSSLKNLGECTGGKNGIAADITTAKGYVKSVT TSNGAITVKGDGTLANMEYILQATGNAATGVTWTTCKGTDAS LFPANFCGSVTQ |
| 22 | MGSSHHHHHSSGLVPRGSHMTKKAAVSELLQASAPYKADVEL CLVRSDYKLYNKNSSSTLKNLGERHTCTGGKNGIAADITTAKG YVKSVTTSNGAITVKGDGTLANMEYILQATGNAATGVTWTTC KGTDASLFPANFCGSVTQ |
| 23 | MGSSHHHHHSSGLVPRGSHMTKKAAVSELLQASAPYKADVEL CVTSTNETTNCTGGKNGIAADITTAKGYVKSVTTSNGAITVKG DGTLANMEYILQATGNAATGVTWTTCRSDYKLYNKNSSTLKN LGECGSVTQ |
| 24 | MGSSHHHHHSSGLVPRGSHMTKKAAVSELLQASAPYKADVEL CVTSTNEILNCTGGKNGIAADITTAKGYVKSVTTSNGAITVKG DGTLANMEYTTQATGNAATGVTWTTCLVRSDYKLYNKNSSTL KNLGERHTCGSVTQ |
| 25 | MGSSHHHHHSSGLVPRGSHMTKKAAVSELLQASAPYKADVEL CVTSTNTTNCTGGKNGIAADITTAKGYVKSVTTSNGAITVKG DGTLANMEYILQATGNAATGVTWTTCKGTDASLFPANFCGSV TQRSDYKLYNKNSSTLKNLGE |
| 26 | MGSSHHHHHSSGLVPRGSHMTKKAAVSELLQASAPYKADVEL CVTSTNTTNCTGGKNGIAADITTAKGYVKSVTTSNGAITVKG DGTLANMEYILQATGNAATGVTWTTCKGTDASLFPANFCGSV TQLVRSDYKLYNKNSSTLKNLGERHT |
| 27 | MGSSHHHHHSSGLVPRGSHMTKKAAVSELLQASAPYKADVEL CRSDYKFYDNKRIDCTGGKNGIAADITTAKGYVKSVTTSNGAI TVKGDGTLANMEYILQATGNAATGVTWTTCKGTDASLFPANF CGSVTQ |
| 28 | MGSSHHHHHSSGLVPRGSHMTKKAAVSELLQASAPYKADVEL CLVRSDYKFYDNKRIDRHTCTGGKNGIAADITTAKGYVKSVTT SNGAITVKGDGTLANMEYILQATGNAATGVTWTTCKGTDASL FPANFCGSVTQ |
| 29 | MGSSHHHHHSSGLVPRGSHMTKKAAVSELLQASAPYKADVEL CVTSTNETTNCTGGKNGIAADITTAKGYVKSVTTSNGAITVKG DGTLANMEYILQATGNAATGVTWTTCRSDYKFYDNKRIDCGS VTQ |
| 30 | MGSSHHHHHSSGLVPRGSHMTKKAAVSELLQASAPYKADVEL CVTSTNTTNCTGGKNGIAADITTAKGYVKSVTTSNGAITVKG DGTLANMEYILQATGNAATGVTWTTCLVRSDYKFYDNKRIDR HTCGSVTQ |
| 31 | MGSSHHHHHSSGLVPRGSHMTKKAAVSELLQASAPYKADVEL CVTSTNTTNCTGGKNGIAADITTAKGYVKSVTTSNGAITVKG DGTLANMEYILQATGNAATGVTWTTCKGTDASLFPANFCGSV TQRSDYKFYDNKRID |
| 32 | MGSSHHHHHSSGLVPRGSHMTKKAAVSELLQASAPYKADVEL CVTSTNTTNCTGGKNGIAADITTAKGYVKSVTTSNGAITVKG DGTLANMEYILQATGNAATGVTWTTCKGTDASLFPANFCGSV TQLVRSDYKFYDNKRIDRHT |

Additional exemplary chimeric proteins of the invention have the amino acid sequences as set out in Table 3 below. These chimeric proteins have been expressed by *E. coli* and purified using a HIS-tag, as described above. The chimeric proteins set out in Table 3 have the His tag sequence removed for use as an immunogen. The chimeric protein having the amino acid sequence of SEQ ID NO: 56 was used in the studies described in Example 5.

TABLE 3

| SEQ ID NO: | Chimeric Protein Amino Acid Sequence |
|---|---|
| 54 | GSHMTKKAAVSELLQASAPYKADVELCLVRSDYKFYEDANGT RDHKKGRHTCTGGKNGIAADITTAKGYVKSVTTSNGAITVKG DGTLANMEYILQATGNAATGVTWTTTCKGTDASLFPANFCGS VTQ |
| 55 | GSHMTKKAAVSELLQASAPYKADVELCVYSTNETTNCTGGKN GIAADITTAKGYVKSVTTSNGAITVKGDGTLANMEYILQATGN AATGVTWTTTCLVRSDYKFYEDANGTRDHKKGRHTCGSVTQ |
| 56 | GSHMTKKAAVSELLQASAPYKADVELCVYSTNETTNCTGGKN GIAADITTAKGYVKSVTTSNGAITVKGDGTLANMEYILQATGN AATGVTWTTTCKGTDASLFPANFCGSVTQLVRSDYKFYEDAN GTRDHKKGRHT |
| 57 | GSHMLVRSDYKFYEDANGTRDHKKGRHTGPSLKLTKKAAVSE LLQASAPYKADVELCVYSTNETTNCTGGKNGIAADITTAKGYV KSVTTSNGAITVKGDGTLANMEYILQATGNAATGVTWTTTCK GTDASLFPANFCGSVTQ |

EXAMPLE 2

Immunogenicity of Chimeric Proteins

Rabbits or chinchillas are immunized with the chimeric proteins. Rabbits receive an initial immunizing dose of 500 µg of a chimeric protein in complete Freund's adjuvant. The rabbits receive a second dose of 400 µg of the chimeric protein 21 days later. The rabbits receive a third dose of chimeric protein in complete Freund's adjuvant 42 days after the initial immunizing dose with 400 µg of the same peptide in either IFA or PBS (one rabbit per diluent). Sera are obtained 3 weeks after each dose. Chinchillas receive an initial immunizing dose of 10 µg of the chimeric protein in the adjuvant monophosphoryl lipid A (MPL). One month (~30 days) later, chinchillas receive a second identical dose. The third and final dose is delivered 30 days after the second dose. Sera are obtained ~10-14 days after each dose. The sera from all animals are assessed for titer and specificity against the LB1 peptide (40-mer), LB1(1), PilA protein and the chimeric proteins, by ELISA, Western blot and biosensor. Antisera are also tested against whole bacteria via flow cytometry (FACS) analysis.

EXAMPLE 3

Evaluating Passive Immunization

The protection conferred by an animal's immune response directed against the chimeric proteins of the invention is determined in a chinchilla model of experimental otitis media. Chinchillas are passively immunized with 5 ml/kg hyperimmune chinchilla or human serum directed against a chimeric protein of the invention. Control chinchillas receive normal chinchilla serum or normal human serum. Next the chinchillas receive first a viral co-pathogen intranasally, then a week later, an intranasal challenge with the NTHi bacteria. The chinchillas are examined and rated daily or every 2 days for up to 35 days after bacterial challenge. Immunized chinchillas receiving immune chinchilla or human serum display reduced tympanic membrane pathology and reduced or absent signs of infection of the middle ear space as determined by both video otoscopy and tympanometry. In this assay, the presence of middle ear fluids in chinchillas receiving chinchilla or human anti-chimeric protein serum is reduced when compared to controls.

EXAMPLE 4

Evaluating Active Immunization

Cohorts of 5-10 chinchillas each are actively immunized with either a saline control preparation, an adjuvant-only preparation, or one of the chimeric proteins of the invention that has been admixed with an appropriate adjuvant. The immunogens are assessed for endotoxin content prior to their use as an immunogen via a chromogenic Amoebocyte Lysate assay which is commercially available from Whittaker Bio-products under the designation QCL-1000. The chinchillas are then subcutaneously injected with 10 µg immunogen in the adjuvant MPL (or another appropriate adjuvant). Then 30 days later they receive 10 µg of the same immunogen in MPL. Thirty days following the second immunization, these animals receive the final immunizing dose. Approximately 10-14 days after the final immunizing dose is delivered, chinchillas are challenged both transbullarly and intranasally with a strain of NTHi. The chinchillas are assessed over a 35-day period for: tympanic membrane pathology by video otoscopic examination and tympanometry; semiquantitation of NTHi recovered via epitympanic tap of the inferior bulla and passive lavage of the nasopharynx; and light microscopic examination of fixed middle ear mucosal epithelium and tympanic membrane for histopathology. For example, chinchillas immunized with the chimeric proteins of the invention will have reduced tympanic membrane pathology, will be free of middle ears effusions or they will contain effusions that are culture-negative, there will be reduced or no biofilm present in the tympanum and there will be minimal thickening of the middle ear mucosa, minimal osteoneogensis and reduced presence of both red blood cells and inflammatory cells in the subepithelial space.

EXAMPLE 5

Evaluation of Chimeric Proteins

The protective efficacy of the chimeric protein having the amino acid sequence of SEQ ID NO: 56 (referred to as "chim-V3" herein) was evaluated using the chinchilla passive-transfer, superinfection model of OM. This chimeric peptide comprised the B-cell epitope of the LB1 peptide (SEQ ID NO: 5) expressed after the C-terminal glutamine residue of recombinant PilA (residues 40-149 of SEQ ID NO: 2). To generate polyclonal antiserum for use in passive transfer efficacy studies, the chim-V3 protein was delivered to a cohort of adult chinchillas with the adjuvant, monophosphoryl lipid A (MPL) plus trehalose dimycolate (Corixa). A timeline depicting the immunization regimen is set out in FIG. 1. To generate immune serum pools, alert prone chinchillas were immunized subcutaneously 3 times with 30 µg of chim-V3 plus 10 µg of MPL or 10 µg MPL alone every 21 days. At day 56, a terminal bleed of the inoculated animals was collected and serum was pooled for transfer to naïve juvenile animals. To study efficacy, a separate cohort of juvenile chinchillas was first challenged with adenovirus on day −7. Six days later (day −1), the pooled anti-chim-V3 immune serum was passively transferred to these adenovirus-compromised animals. The following day (day 0), animals that received anti-chim-V3 serum by passive transfer were challenged with the bacterium, nontypeable *Haemmophilus influenzae*. These animals were then monitored for incidence and severity of disease over a 26-day time-course (relative to bacterial challenge) by daily video otoscopy and tympanometry as well as Xenogen in vivo imaging every other day.

The titer of anti-chim-V3 antibody was measured in the immune serum collected from the inoculated animals using an ELISA. This analysis demonstrated that the collected antiserum contained antibodies specific for the chim-V3 protein. The presence of anti-chim-V3 antibodies in the collected antiserum as also confirmed using Western blot analysis.

FACS analysis was used to measure the ability of serum immunoglobulins from immunized animals to recognize surface exposed native structures expressed by NTHi 86-028 NP. NTHi bacteria were incubated with chim-V3 antiserum, washed, then incubated with naïve or immune FITC-Protein A, washed and analyzed by FACS analysis. Inoculation with the chim-V3 protein induced a significant increase in antibodies that were capable of recognizing the NTHi surface proteins or chim-V3 protein. The data obtained were dependent on both antibody titer and avidity as well as relative expression of both the type IV pilus and the OMP P5-homologous adhesion by NTHi when grown in vitro.

The luminescent reporter NTHi 86-028 NP pKMLN-1 was used to detect NTHi infection in the animals inoculated with chim-V3 protein using Xenogen in vivo real-time imagining. Growth curves of the luminescent strain NTHi 86-028 NP pKMLN-1 and the parental strain NTHi 86-028 demonstrated that growth of the luminescent NTHi strain was comparable to the parental strain. Luminescent imaging of NTHi residing in the nasopharynx of the inoculated animals was readily accomplished however, due to the microaerophilic nature of the diseased middle ear, luminescence of NTHi present in the middle ear could not be monitored over the entire disease course because the luminescence is dependent on the availability of oxygen. Animals were monitored every other day for the presence of luminescent bacteria, and if bacteria were detected, this was recorded as a luminescent event. Luminescent infection was detected at least six days after challenge in the inoculated animals. The total number of luminescent events in the chim-V3 inoculated animals was less than the total number of luminescent events in the control animals (inoculated with MPL only).

Throughout the course of the study, daily video otoscopy and tympanometry was used to determine the percent of chinchilla middle ears with OM. Inoculation with chim-V3 caused 53% reduction in the number of animals with middle ears having OM as compared to control animals (inoculated with MPL only).

All of these studies demonstrate that the chim-V3 protein was immunogenic and anti-chim-V3 antibodies were protective in the chinchilla passive transfer-superinfection model of OM.

We claim:

1. A method for eliciting an immune response to NTHi bacteria comprising administering an immunogenic dose of a chimeric protein to a patient at risk of NTHi bacterial infection wherein the chimeric protein comprises i) an immunogenic PilA peptide selected from the group consisting of the amino acid sequence of SEQ ID NO: 6, SEQ ID NO: 7, SEQ ID NO: 8 or residues 40 to 149 of SEQ ID NO: 2 and ii) the LB 1 peptide selected from the group consisting of the amino acid sequence of SEQ ID NO: 4 and SEQ ID NO: 5, wherein the LB 1 peptide is inserted before the immunogenic PilA peptide.

2. The method of claim 1 wherein the NTHi infection is in the middle ear, nasopharynx or lower airway.

3. The method of claim 1 wherein the NTHi bacterial infection involves a pathological condition selected from the group consisting of otitis media, pneumonia, sinusitis, septicemia, endocarditis, epiglottitis, septic arthritis, meningitis, sepsis, salpingitis, epiglottis, pericardis, cellulitis, osteomyelitis, endocarditis, cholecystitis, intraabdominal infections, urinary tract infection, mastoiditis, aortic graft infection, conjunctitivitis, Brazilian purpuric fever, occult bacteremia, chronic obstructive pulmonary disease, chronic bronchitis, bronchietasis and cystic fibrosis.

4. The method of claim 1 wherein the immunogenic dose of the chimeric polypeptide is administered using a route of administration selected from the group consisting of parenteral, intravenous, oral, buccal, nasal, pulmonary, rectal, intranasal, transdermal, subcutaneous, intramuscular or vaginal administration.

5. The method of claim 1 wherein PilA peptide comprises residues 40-149 of SEQ ID NO: 2 and wherein the LB1 peptide comprises SEQ ID NO: 4.

6. The method of claim 1 wherein the chimeric protein comprises the amino acid sequence of SEQ ID NO: 57.

* * * * *

UNITED STATES PATENT AND TRADEMARK OFFICE
CERTIFICATE OF CORRECTION

PATENT NO. : 8,741,304 B2  
APPLICATION NO. : 13/608500  
DATED : June 3, 2014  
INVENTOR(S) : Lauren O. Bakaletz et al.

Page 1 of 1

It is certified that error appears in the above-identified patent and that said Letters Patent is hereby corrected as shown below:

On the Title Page

Item (73), in Column 1, "Hospital" should be -- Hospital, Columbus, OH --.

At Column 1, below "Related U.S. Application Data", in Line 1, Item "(60)" should be Item -- (63) --.

In the Claims

At Column 78, Line 46, "pericardis," should be -- pericarditis, --.

At Column 78, Lines 48-49, "conjunctitivitis," should be -- conjunctivitis, --.

At Column 78, Line 51, "bronchietasis" should be -- bronchiectasis --.

Signed and Sealed this  
Twenty-first Day of July, 2015

Michelle K. Lee  
*Director of the United States Patent and Trademark Office*

SEQUENCE LISTING

```
<160> NUMBER OF SEQ ID NOS: 57

<210> SEQ ID NO 1
<211> LENGTH: 4345
<212> TYPE: DNA
<213> ORGANISM: H. influenzae
<220> FEATURE:
```

```
<221> NAME/KEY: CDS
<222> LOCATION: (403)..(849)

<400> SEQUENCE: 1
gcgatcatta aaattgacat attgcgtaat tcgcccattt cgttcgatca aacaatgtgc      60
tgaaacacgc atttgataaa tttctgcaaa ataaggatga atcttaggat ctaattttcc     120
ttgaaaaaaa tcatccacat atccgccgcc aaattgttct ggcggcagac taatataatg    180
aataaccaat aaggaaatat cctgtggatt tgggcgttta tcgaagtgag gtgactgaat    240
ttgccgacaa tccaatatac cttgttcaat atcttttagt ttttgcatac ttttttcctt    300
tttttgcgat caggatcgca gaaaaagtgc ggtcaatttt acaaacaaat ttttcctttt    360
cacaatgtcg tcgctaacaa aggcttaata aaggaaaat ga atg aaa cta aca         414
                                              Met Lys Leu Thr
                                                1 aca cag caa acc ttg aaa aaa ggg ttt aca tta ata gag cta atg att       462
Thr Gln Gln Thr Leu Lys Lys Gly Phe Thr Leu Ile Glu Leu Met Ile
 5                  10                  15                  20 gtg att gca att att gct att tta gcc act atc gca att ccc tct tat       510
Val Ile Ala Ile Ile Ala Ile Leu Ala Thr Ile Ala Ile Pro Ser Tyr
                 25                  30                  35 caa aat tat act aaa aaa gca gcg gta tct gaa tta ctg caa gcg tca       558
Gln Asn Tyr Thr Lys Lys Ala Ala Val Ser Glu Leu Leu Gln Ala Ser
             40                  45                  50 gcg cct tat aag gct gat gtg gaa tta tgt gta tat agc aca aat gaa       606
Ala Pro Tyr Lys Ala Asp Val Glu Leu Cys Val Tyr Ser Thr Asn Glu
         55                  60                  65 aca aca aac tgt acg ggt gga aaa aat ggt att gca gca gat ata acc       654
Thr Thr Asn Cys Thr Gly Gly Lys Asn Gly Ile Ala Ala Asp Ile Thr
 70                  75                  80 aca gca aaa ggc tat gta aaa tca gtg aca aca agc aac ggt gca ata       702
Thr Ala Lys Gly Tyr Val Lys Ser Val Thr Thr Ser Asn Gly Ala Ile
 85                  90                  95                 100 aca gta aaa ggg gat ggc aca ttg gca aat atg gaa tat att ttg caa       750
Thr Val Lys Gly Asp Gly Thr Leu Ala Asn Met Glu Tyr Ile Leu Gln
                105                 110                 115 gct aca ggt aat gct gca aca ggt gta act tgg aca aca act tgc aaa       798
Ala Thr Gly Asn Ala Ala Thr Gly Val Thr Trp Thr Thr Thr Cys Lys
            120                 125                 130 gga acg gat gcc tct tta ttt cca gca aat ttt tgc gga agt gtc aca       846
Gly Thr Asp Ala Ser Leu Phe Pro Ala Asn Phe Cys Gly Ser Val Thr
        135                 140                 145 caa tgacgagcta tgctttactt catactcagc gtgtaaccgc tcaaaatggc            899
Gln gagatcttta cgatctcgcc agattatgg gaacgcaatc agcagcaaca atccttgctc     959
ttgcggtatt ttgctttgcc acttaaagaa gaaaataatc gtctttggct aggggttgat   1019
tctctctcca atctttcagc ttgtgaaacc attgcgttta acaggaaa acctgtcgaa     1079 ccaattttgt tagaaagcag ccaactcaaa gaactgttac aacaacttac tccgcaccaa   1139
atgcaagtgg aagagcaagt taaattctat caacatcaag aaacccattt tgaacaagaa   1199
gatgatgaac ctgttatccg cttacttaat cagatttttg aatctgcctt acaaaaaaat   1259
gcctctgata ttcatttaga aaccttggct gatcagtttc aagtgcggtt tagaattgat   1319
ggtgttttac aaccacaacc cttaataagc aaaatattcg ccaatcgtat tatttcacgc   1379
ttaaaattac tggctaaatt agatattagt gaaaatcgac ttccacaaga tggacgatt   1439 caatttaaaa ccacttttc cgatattctt gattttcgcc tttcaacctt accaacccat   1499
```

```
tggggcgaaa aaatcgtgtt gcgagcgcaa caaaataaac ctgtagaact tagctttgct    1559
gaactgggta tgaccgaaaa tcagcaacaa gcatttcaac gctcacttag ccagccacaa    1619
ggattaattt tagtaaccgg ccccacagga agtgggaaaa gtatctcgct ttacaccgca    1679
cttcagtggc taaatacgcc tgataaacat attatgaccg ctgaagatcc cattgaaatt    1739
gaacttgatg gtattattca aagccaaatt aatccgcaga ttggattaga ttttagccgt    1799
ctattgcgtg ctttttttacg tcaagatccc gacatcatta tgctaggtga aattcgagat    1859
gaagaaagtg caaggattgc actacgtgcc gctcaaacgg gacatttggt gctttcaact    1919
ttacatacca atgatgcaat atctgccatt tctcgcttac aacaactcgg tattcaacaa    1979
catgaaattg aaaacagttt actactcgtc attgcacagc gtcttgtacg aaaaatctgt    2039
ccaaagtgcg gtgaaatttt aataaattct tgtgattgcc atcaaggtta tcgagggcga    2099
atcggcgtgt atcaattttct acattggcaa cagaatggct atcaaacgga ttttgagaat    2159
ttacagagag gtggtttgga aaaagttagc caaggcataa cagatgagaa agaaattgaa    2219
cgtgtgttag gtaaaaactc atgactaaaa aactctttta ttatcaaggt agtaacgcat    2279
taaatcagaa acaaaaaggc tcaattattg cggatacgaa acaacaagcg cactttcagt    2339
taataagccg cgggcttact cacatcaaat tacaacaaaa ctggcaattt ggggcaaaac    2399
ccaaaaattc agaaatcagt gaattactca atcaattagc gacattgcta cagtccgtaa    2459
ttccgttaaa aaacagccta caaattttgc aacaaaattg tactcaaatt atgctcaaca    2519
aatggcttga cgactgcttt caatccattg aatctggctt agcattctca caagccattg    2579
aacaacaagg aaaatatctc acacaacaag aaattcaact gattcaagtg ggagaaatga    2639
caggaaaact tgccgtagtt tgtaaaaaaa tagccacgca ccgtagtcaa tctttggctt    2699
tacaacgcaa attacagaaa attatgttat atccctcaat ggtattggga atttctctat    2759
tattgacact cgcattactg ctttttatcg cgcctcaatt tgctgaaatg tacagtggca    2819
ataatgcgga gttaccaaca ataaccgcaa tattgctctc aatatctaat ttccttaagc    2879
aaaatattgg cattttgcta ttttttcgttt tgagttttttt tctattttat tatttctatc    2939
taaaacgcca gacttggttt catcaaaaga aaaatcaact tatttctatc acgcctattt    2999
ttggcacaat tcaaaagctt tcacgtttag tgaactttag tcaaagttta caaattatgt    3059
tgcaggccgc cgtaccgctt aatcaggcac tagacagttt tcttcctcgc acacaaactt    3119
ggcaaaccaa gaaaacgctt gtaaacgata tggtattaga taaagaagtg cggtcaattt    3179
tgcaatgggt ttctcaaggc tatgcgtttt ctaatagcgt aagtagcgat cttttcccga    3239
tggaagcaca acaaatgcta caaattggcg aacaaagcgg aaaactcgct ttgatgctag    3299
agcatatcgc agataattac caagaaaaac ttaatcatca aattgactta ctctcacaaa    3359
tgctagaacc attaatgatg gtaatcatcg gcagtctgat tgggattatt atgatgggaa    3419
tgtatttacc tatctttaat atgggatcag ttattcaatg atttacttca caatgttttt    3479
attaggcggc atcttaggga tcgcattgtg gttctaccta tctggttttta ttacgcattt    3539 gcagcaagag atttatgcga cttacgttga attatttcca caaaacagtt ctccatttca    3599
accgcacttt gcctctattc aacaaaaaaa gtgcggtcat attttgaggt attttttttag    3659 tattggggtt ggatttatat tttttacaaat tgccttcaaa gattctattt ttactgtatg    3719
gatcggactc acacttatta ttctttggac aatcagttat cttgattggc actatcaact    3779
tatttctacg acaccctgtt tatggttact tactctcggt ttatttggcg cagacaataa    3839
cttttcattg ctaacgttat ctgaaagcat aaaaagtgcg gctagttttt ttattgtttt    3899
```

```
ctacgcaatc tattggattg caaaatgtta ttatagaaaa gaagcctttg gacggggaga    3959
ttattggcta gcaatggcat taggaagttt tattcattta gaaaccttac cgcactttt     4019 attattagcc tcagtgcttg aatatgttt ttcgcttatt cataaaaaga aaaagaatt      4079 tatacctttt gccccttta tgaacttatc ggctatcatt atttatctcg tcaaatatta    4139
cggatattaa aaggggaaa acataatatt tttcccttgt tcttcataga agtgcggttg    4199
tttttacgaa cgtttcatca cttcaaaaaa ctcttcgttg gttttcgcca tcatcagctt   4259
atcaatcaag aattccattg catccacttc atccattgga ttaagaatct tacgaagaat   4319 ccacatttt tgtaattcgt ccgctg                                         4345
```

<210> SEQ ID NO 2
<211> LENGTH: 149
<212> TYPE: PRT
<213> ORGANISM: H. influenzae

<400> SEQUENCE: 2

```
Met Lys Leu Thr Thr Gln Gln Thr Leu Lys Lys Gly Phe Thr Leu Ile
1               5                   10                  15
Glu Leu Met Ile Val Ile Ala Ile Ile Ala Ile Leu Ala Thr Ile Ala
                20                  25                  30
Ile Pro Ser Tyr Gln Asn Tyr Thr Lys Lys Ala Ala Val Ser Glu Leu
            35                  40                  45
Leu Gln Ala Ser Ala Pro Tyr Lys Ala Asp Val Glu Leu Cys Val Tyr
        50                  55                  60
Ser Thr Asn Glu Thr Thr Asn Cys Thr Gly Gly Lys Asn Gly Ile Ala
65                  70                  75                  80
Ala Asp Ile Thr Thr Ala Lys Gly Tyr Val Lys Ser Val Thr Thr Ser
                85                  90                  95
Asn Gly Ala Ile Thr Val Lys Gly Asp Gly Thr Leu Ala Asn Met Glu
            100                 105                 110
Tyr Ile Leu Gln Ala Thr Gly Asn Ala Ala Thr Gly Val Thr Trp Thr
        115                 120                 125
Thr Thr Cys Lys Gly Thr Asp Ala Ser Leu Phe Pro Ala Asn Phe Cys
    130                 135                 140
Gly Ser Val Thr Gln
145
```

<210> SEQ ID NO 3
<211> LENGTH: 131
<212> TYPE: PRT
<213> ORGANISM: H. influenzae

<400> SEQUENCE: 3

```
Met Gly Ser Ser His His His His His His Ser Ser Gly Leu Val Pro
1               5                   10                  15
Arg Gly Ser His Met Thr Lys Lys Ala Ala Val Ser Glu Leu Leu Gln
                20                  25                  30
Ala Ser Ala Pro Tyr Lys Ala Asp Val Glu Leu Cys Val Tyr Ser Thr
            35                  40                  45
Asn Glu Thr Thr Asn Cys Thr Gly Gly Lys Asn Gly Ile Ala Ala Asp
        50                  55                  60
Ile Thr Thr Ala Lys Gly Tyr Val Lys Ser Val Thr Thr Ser Asn Gly
65                  70                  75                  80
Ala Ile Thr Val Lys Gly Asp Gly Thr Leu Ala Asn Met Glu Tyr Ile
                85                  90                  95
```

```
Leu Gln Ala Thr Gly Asn Ala Ala Thr Gly Val Thr Trp Thr Thr Thr
                100                 105                 110

Cys Lys Gly Thr Asp Ala Ser Leu Phe Pro Ala Asn Phe Cys Gly Ser
        115                 120                 125

Val Thr Gln
    130

<210> SEQ ID NO 4
<211> LENGTH: 19
<212> TYPE: PRT
<213> ORGANISM: Artificial sequence
<220> FEATURE:
<223> OTHER INFORMATION: Synthetic Peptide

<400> SEQUENCE: 4

Arg Ser Asp Tyr Lys Phe Tyr Glu Asp Ala Asn Gly Thr Arg Asp His
1               5                   10                  15

Lys Lys Gly

<210> SEQ ID NO 5
<211> LENGTH: 24
<212> TYPE: PRT
<213> ORGANISM: Artificial sequence
<220> FEATURE:
<223> OTHER INFORMATION: Synthetic Peptide

<400> SEQUENCE: 5

Leu Val Arg Ser Asp Tyr Lys Phe Tyr Glu Asp Ala Asn Gly Thr Arg
1               5                   10                  15

Asp His Lys Lys Gly Arg His Thr
            20

<210> SEQ ID NO 6
<211> LENGTH: 22
<212> TYPE: PRT
<213> ORGANISM: Artificial Sequence
<220> FEATURE:
<223> OTHER INFORMATION: Synthetic Peptide

<400> SEQUENCE: 6

Arg Ser Asp Tyr Lys Leu Tyr Asn Lys Asn Ser Ser Asn Ser Thr
1               5                   10                  15

Leu Lys Asn Leu Gly Glu
            20

<210> SEQ ID NO 7
<211> LENGTH: 19
<212> TYPE: PRT
<213> ORGANISM: Artificial sequence
<220> FEATURE:
<223> OTHER INFORMATION: Synthetic Peptide

<400> SEQUENCE: 7

Arg Ser Asp Tyr Lys Leu Tyr Asn Lys Asn Ser Ser Thr Leu Lys Asp
1               5                   10                  15

Leu Gly Glu

<210> SEQ ID NO 8
<211> LENGTH: 13
<212> TYPE: PRT
<213> ORGANISM: Artificial sequence
<220> FEATURE:
<223> OTHER INFORMATION: Synthetic Peptide

<400> SEQUENCE: 8
```

Arg Ser Asp Tyr Lys Phe Tyr Asp Asn Lys Arg Ile Asp
1               5                   10

<210> SEQ ID NO 9
<211> LENGTH: 139
<212> TYPE: PRT
<213> ORGANISM: Artificial sequence
<220> FEATURE:
<223> OTHER INFORMATION: Chimeric protein

<400> SEQUENCE: 9

Met Gly Ser Ser His His His His Ser Gly Leu Val Pro Arg
1               5                   10                  15

Gly Ser His Met Thr Lys Lys Ala Ala Val Ser Glu Leu Leu Gln Ala
            20                  25                  30

Ser Ala Pro Tyr Lys Ala Asp Val Glu Leu Cys Arg Ser Asp Tyr Lys
        35                  40                  45

Phe Tyr Glu Asp Ala Asn Gly Thr Arg Asp His Lys Lys Gly Cys Thr
    50                  55                  60

Gly Gly Lys Asn Gly Ile Ala Ala Asp Ile Thr Thr Ala Lys Gly Tyr
65                  70                  75                  80

Val Lys Ser Val Thr Thr Ser Asn Gly Ala Ile Thr Val Lys Gly Asp
                85                  90                  95

Gly Thr Leu Ala Asn Met Glu Tyr Ile Leu Gln Ala Thr Gly Asn Ala
            100                 105                 110

Ala Thr Gly Val Thr Trp Thr Thr Cys Lys Gly Thr Asp Ala Ser Leu
        115                 120                 125

Phe Pro Ala Asn Phe Cys Gly Ser Val Thr Gln
    130                 135

<210> SEQ ID NO 10
<211> LENGTH: 143
<212> TYPE: PRT
<213> ORGANISM: Artificial sequence
<220> FEATURE:
<223> OTHER INFORMATION: Chimeric Protein

<400> SEQUENCE: 10

Met Gly Ser Ser His His His His Ser Gly Leu Val Pro Arg
1               5                   10                  15

Gly Ser His Met Thr Lys Lys Ala Ala Val Ser Glu Leu Leu Gln Ala
            20                  25                  30

Ser Ala Pro Tyr Lys Ala Asp Val Glu Leu Cys Leu Val Arg Ser Asp
        35                  40                  45

Tyr Lys Phe Tyr Glu Asp Ala Asn Gly Thr Arg Asp His Lys Lys Gly
    50                  55                  60

His Thr Cys Thr Gly Gly Lys Asn Gly Ile Ala Ala Asp Ile Thr Thr
65                  70                  75                  80

Ala Lys Gly Tyr Val Lys Ser Val Thr Thr Ser Asn Gly Ala Ile Thr
                85                  90                  95

Val Lys Gly Asp Gly Thr Leu Ala Asn Met Glu Tyr Ile Leu Gln Ala
            100                 105                 110

Thr Gly Asn Ala Ala Thr Gly Val Thr Trp Thr Thr Cys Lys Gly Thr
        115                 120                 125

Asp Ala Ser Leu Phe Pro Ala Asn Phe Cys Gly Ser Val Thr Gln
    130                 135                 140

<210> SEQ ID NO 11

```
<211> LENGTH: 136
<212> TYPE: PRT
<213> ORGANISM: Artificial sequence
<220> FEATURE:
<223> OTHER INFORMATION: Chimeric Protein

<400> SEQUENCE: 11

Met Gly Ser Ser His His His His Ser Ser Gly Leu Val Pro Arg
1               5                   10                  15

Gly Ser His Met Thr Lys Lys Ala Ala Val Ser Glu Leu Leu Gln Ala
            20                  25                  30

Ser Ala Pro Tyr Lys Ala Asp Val Glu Leu Cys Val Thr Ser Thr Asn
        35                  40                  45

Glu Thr Thr Asn Cys Thr Gly Gly Lys Asn Gly Ile Ala Ala Asp Ile
    50                  55                  60

Thr Thr Ala Lys Gly Tyr Val Lys Ser Val Thr Ser Asn Gly Ala
65                  70                  75                  80

Ile Thr Val Lys Gly Asp Gly Thr Leu Ala Asn Met Glu Tyr Ile Leu
                85                  90                  95

Gln Ala Thr Gly Asn Ala Ala Thr Gly Val Thr Trp Thr Thr Cys Arg
            100                 105                 110

Ser Asp Tyr Lys Phe Tyr Glu Asp Ala Asn Gly Thr Arg Asp His Lys
        115                 120                 125

Lys Gly Cys Gly Ser Val Thr Gln
    130                 135

<210> SEQ ID NO 12
<211> LENGTH: 141
<212> TYPE: PRT
<213> ORGANISM: Artificial sequence
<220> FEATURE:
<223> OTHER INFORMATION: Chimeric Protein

<400> SEQUENCE: 12

Met Gly Ser Ser His His His His His Ser Ser Gly Leu Val Pro Arg
1               5                   10                  15

Gly Ser His Met Thr Lys Lys Ala Ala Val Ser Glu Leu Leu Gln Ala
            20                  25                  30

Ser Ala Pro Tyr Lys Ala Asp Val Glu Leu Cys Val Thr Ser Thr Asn
        35                  40                  45

Glu Thr Thr Asn Cys Thr Gly Gly Lys Asn Gly Ile Ala Ala Asp Ile
    50                  55                  60

Thr Thr Ala Lys Gly Tyr Val Lys Ser Val Thr Ser Asn Gly Ala
65                  70                  75                  80

Ile Thr Val Lys Gly Asp Gly Thr Leu Ala Asn Met Glu Tyr Ile Leu
                85                  90                  95

Gln Ala Thr Gly Asn Ala Ala Thr Gly Val Thr Trp Thr Thr Cys Leu
            100                 105                 110

Val Arg Ser Asp Tyr Lys Phe Tyr Glu Asp Ala Asn Gly Thr Arg Asp
        115                 120                 125

His Lys Lys Gly Arg His Thr Cys Gly Ser Val Thr Gln
    130                 135                 140

<210> SEQ ID NO 13
<211> LENGTH: 148
<212> TYPE: PRT
<213> ORGANISM: Artificial sequence
<220> FEATURE:
<223> OTHER INFORMATION: Chimeric Protein
```

<400> SEQUENCE: 13

Met Gly Ser Ser His His His His Ser Gly Leu Val Pro Arg
1               5                   10                  15

Gly Ser His Met Thr Lys Lys Ala Ala Val Ser Glu Leu Leu Gln Ala
            20                  25                  30

Ser Ala Pro Tyr Lys Ala Asp Val Glu Leu Cys Val Thr Ser Thr Asn
        35                  40                  45

Glu Thr Thr Asn Cys Thr Gly Gly Lys Asn Gly Ile Ala Ala Asp Ile
50                  55                  60

Thr Thr Ala Lys Gly Tyr Val Lys Ser Val Thr Thr Ser Asn Gly Ala
65                  70                  75                  80

Ile Thr Val Lys Gly Asp Gly Thr Leu Ala Asn Met Glu Tyr Ile Leu
                85                  90                  95

Gln Ala Thr Gly Asn Ala Ala Thr Gly Val Thr Trp Thr Thr Cys Lys
                100                 105                 110

Gly Thr Asp Ala Ser Leu Phe Pro Ala Asn Phe Cys Gly Ser Val Thr
            115                 120                 125

Gln Arg Ser Asp Tyr Lys Phe Tyr Glu Asp Ala Asn Gly Thr Arg Asp
        130                 135                 140

His Lys Lys Gly
145

<210> SEQ ID NO 14
<211> LENGTH: 153
<212> TYPE: PRT
<213> ORGANISM: Artificial sequence
<220> FEATURE:
<223> OTHER INFORMATION: Chimeric Protein

<400> SEQUENCE: 14

Met Gly Ser Ser His His His His Ser Gly Leu Val Pro Arg
1               5                   10                  15

Gly Ser His Met Thr Lys Lys Ala Ala Val Ser Glu Leu Leu Gln Ala
            20                  25                  30

Ser Ala Pro Tyr Lys Ala Asp Val Glu Leu Cys Val Thr Ser Thr Asn
        35                  40                  45

Glu Thr Thr Asn Cys Thr Gly Gly Lys Asn Gly Ile Ala Ala Asp Ile
50                  55                  60

Thr Thr Ala Lys Gly Tyr Val Lys Ser Val Thr Thr Ser Asn Gly Ala
65                  70                  75                  80

Ile Thr Val Lys Gly Asp Gly Thr Leu Ala Asn Met Glu Tyr Ile Leu
                85                  90                  95

Gln Ala Thr Gly Asn Ala Ala Thr Gly Val Thr Trp Thr Thr Cys Lys
                100                 105                 110

Gly Thr Asp Ala Ser Leu Phe Pro Ala Asn Phe Cys Gly Ser Val Thr
            115                 120                 125

Gln Leu Val Arg Ser Asp Tyr Lys Phe Tyr Glu Asp Ala Asn Gly Thr
        130                 135                 140

Arg Asp His Lys Lys Gly Arg His Thr
145                 150

<210> SEQ ID NO 15
<211> LENGTH: 142
<212> TYPE: PRT
<213> ORGANISM: Artificial sequence
<220> FEATURE:
<223> OTHER INFORMATION: Chimeric Protein

<400> SEQUENCE: 15

```
Met Gly Ser Ser His His His His Ser Ser Gly Leu Val Pro Arg
1               5                   10                  15

Gly Ser His Met Thr Lys Lys Ala Ala Val Ser Glu Leu Leu Gln Ala
            20                  25                  30

Ser Ala Pro Tyr Lys Ala Asp Val Glu Leu Cys Arg Ser Asp Tyr Lys
        35                  40                  45

Leu Tyr Asn Lys Asn Ser Ser Asn Ser Thr Leu Lys Asn Leu Gly
50                  55                  60

Glu Cys Thr Gly Gly Lys Asn Gly Ile Ala Ala Asp Ile Thr Thr Ala
65                  70                  75                  80

Lys Gly Tyr Val Lys Ser Val Thr Thr Ser Asn Gly Ala Ile Thr Val
                85                  90                  95

Lys Gly Asp Gly Thr Leu Ala Asn Met Glu Tyr Ile Leu Gln Ala Thr
            100                 105                 110

Gly Asn Ala Ala Thr Gly Val Thr Trp Thr Thr Cys Lys Gly Thr Asp
        115                 120                 125

Ala Ser Leu Phe Pro Ala Asn Phe Cys Gly Ser Val Thr Gln
    130                 135                 140
```

<210> SEQ ID NO 16
<211> LENGTH: 147
<212> TYPE: PRT
<213> ORGANISM: Artificial sequence
<220> FEATURE:
<223> OTHER INFORMATION: Chimeric Protein

<400> SEQUENCE: 16

```
Met Gly Ser Ser His His His His His Ser Ser Gly Leu Val Pro Arg
1               5                   10                  15

Gly Ser His Met Thr Lys Lys Ala Ala Val Ser Glu Leu Leu Gln Ala
            20                  25                  30

Ser Ala Pro Tyr Lys Ala Asp Val Glu Leu Cys Leu Val Arg Ser Asp
        35                  40                  45

Tyr Lys Leu Tyr Asn Lys Asn Ser Ser Ser Asn Ser Thr Leu Lys Asn
50                  55                  60

Leu Gly Glu Arg His Thr Cys Thr Gly Gly Lys Asn Gly Ile Ala Ala
65                  70                  75                  80

Asp Ile Thr Thr Ala Lys Gly Tyr Val Lys Ser Val Thr Thr Ser Asn
                85                  90                  95

Gly Ala Ile Thr Val Lys Gly Asp Gly Thr Leu Ala Asn Met Glu Tyr
            100                 105                 110

Ile Leu Gln Ala Thr Gly Asn Ala Ala Thr Gly Val Thr Trp Thr Thr
        115                 120                 125

Cys Lys Gly Thr Asp Ala Ser Leu Phe Pro Ala Asn Phe Cys Gly Ser
    130                 135                 140

Val Thr Gln
145
```

<210> SEQ ID NO 17
<211> LENGTH: 139
<212> TYPE: PRT
<213> ORGANISM: Artificial sequence
<220> FEATURE:
<223> OTHER INFORMATION: Chimeric Protein

<400> SEQUENCE: 17

```
Met Gly Ser Ser His His His His His Ser Ser Gly Leu Val Pro Arg
```

```
              1               5                  10                 15
Gly Ser His Met Thr Lys Lys Ala Ala Val Ser Glu Leu Leu Gln Ala
            20                  25                 30

Ser Ala Pro Tyr Lys Ala Asp Val Glu Leu Cys Val Thr Ser Thr Asn
            35                  40                 45

Glu Thr Thr Asn Cys Thr Gly Gly Lys Asn Gly Ile Ala Ala Asp Ile
            50                  55                 60

Thr Thr Ala Lys Gly Tyr Val Lys Ser Val Thr Thr Ser Asn Gly Ala
 65                  70                 75                     80

Ile Thr Val Lys Gly Asp Gly Thr Leu Ala Asn Met Glu Tyr Ile Leu
                  85                  90                 95

Gln Ala Thr Gly Asn Ala Ala Thr Gly Val Thr Trp Thr Thr Cys Arg
            100                 105                110

Ser Asp Tyr Lys Leu Tyr Asn Lys Asn Ser Ser Ser Asn Ser Thr Leu
            115                 120                125

Lys Asn Leu Gly Glu Cys Gly Ser Val Thr Gln
            130                 135
```

<210> SEQ ID NO 18
<211> LENGTH: 144
<212> TYPE: PRT
<213> ORGANISM: Artificial sequence
<220> FEATURE:
<223> OTHER INFORMATION: Chimeric Protein

<400> SEQUENCE: 18

```
Met Gly Ser Ser His His His His Ser Ser Gly Leu Val Pro Arg
 1               5                  10                 15

Gly Ser His Met Thr Lys Lys Ala Ala Val Ser Glu Leu Leu Gln Ala
            20                  25                 30

Ser Ala Pro Tyr Lys Ala Asp Val Glu Leu Cys Val Thr Ser Thr Asn
            35                  40                 45

Glu Thr Thr Asn Cys Thr Gly Gly Lys Asn Gly Ile Ala Ala Asp Ile
            50                  55                 60

Thr Thr Ala Lys Gly Tyr Val Lys Ser Val Thr Thr Ser Asn Gly Ala
 65                  70                 75                     80

Ile Thr Val Lys Gly Asp Gly Thr Leu Ala Asn Met Glu Tyr Ile Leu
                  85                  90                 95

Gln Ala Thr Gly Asn Ala Ala Thr Gly Val Thr Trp Thr Thr Cys Leu
            100                 105                110

Val Arg Ser Asp Tyr Lys Leu Tyr Asn Lys Asn Ser Ser Ser Asn Ser
            115                 120                125

Thr Leu Lys Asn Leu Gly Glu Arg His Thr Cys Gly Ser Val Thr Gln
            130                 135                140
```

<210> SEQ ID NO 19
<211> LENGTH: 151
<212> TYPE: PRT
<213> ORGANISM: Artificial sequence
<220> FEATURE:
<223> OTHER INFORMATION: Chimeric Protein

<400> SEQUENCE: 19

```
Met Gly Ser Ser His His His His Ser Ser Gly Leu Val Pro Arg
 1               5                  10                 15

Gly Ser His Met Thr Lys Lys Ala Ala Val Ser Glu Leu Leu Gln Ala
            20                  25                 30

Ser Ala Pro Tyr Lys Ala Asp Val Glu Leu Cys Val Thr Ser Thr Asn
```

```
                35                  40                  45
Glu Thr Thr Asn Cys Thr Gly Gly Lys Asn Gly Ile Ala Ala Asp Ile
 50                  55                  60

Thr Thr Ala Lys Gly Tyr Val Lys Ser Val Thr Ser Asn Gly Ala
 65                  70                  75                  80

Ile Thr Val Lys Gly Asp Gly Thr Leu Ala Asn Met Glu Tyr Ile Leu
                 85                  90                  95

Gln Ala Thr Gly Asn Ala Ala Thr Gly Val Thr Trp Thr Thr Cys Lys
                100                 105                 110

Gly Thr Asp Ala Ser Leu Phe Pro Ala Asn Phe Cys Gly Ser Val Thr
                115                 120                 125

Gln Arg Ser Asp Tyr Lys Leu Tyr Asn Lys Asn Ser Ser Asn Ser
                130                 135                 140

Thr Leu Lys Asn Leu Gly Glu
145                 150
```

<210> SEQ ID NO 20
<211> LENGTH: 156
<212> TYPE: PRT
<213> ORGANISM: Artificial sequence
<220> FEATURE:
<223> OTHER INFORMATION: Chimeric Protein

<400> SEQUENCE: 20

```
Met Gly Ser Ser His His His His Ser Ser Gly Leu Val Pro Arg
 1               5                  10                  15

Gly Ser His Met Thr Lys Lys Ala Ala Val Ser Glu Leu Leu Gln Ala
                 20                  25                  30

Ser Ala Pro Tyr Lys Ala Asp Val Glu Leu Cys Val Thr Ser Thr Asn
                 35                  40                  45

Glu Thr Thr Asn Cys Thr Gly Gly Lys Asn Gly Ile Ala Ala Asp Ile
 50                  55                  60

Thr Thr Ala Lys Gly Tyr Val Lys Ser Val Thr Ser Asn Gly Ala
 65                  70                  75                  80

Ile Thr Val Lys Gly Asp Gly Thr Leu Ala Asn Met Glu Tyr Ile Leu
                 85                  90                  95

Gln Ala Thr Gly Asn Ala Ala Thr Gly Val Thr Trp Thr Thr Cys Lys
                100                 105                 110

Gly Thr Asp Ala Ser Leu Phe Pro Ala Asn Phe Cys Gly Ser Val Thr
                115                 120                 125

Gln Leu Val Arg Ser Asp Tyr Lys Leu Tyr Asn Lys Asn Ser Ser Ser
                130                 135                 140

Asn Ser Thr Leu Lys Asn Leu Gly Glu Arg His Thr
145                 150                 155
```

<210> SEQ ID NO 21
<211> LENGTH: 139
<212> TYPE: PRT
<213> ORGANISM: Artificial sequence
<220> FEATURE:
<223> OTHER INFORMATION: Chimeric Protein

<400> SEQUENCE: 21

```
Met Gly Ser Ser His His His His Ser Ser Gly Leu Val Pro Arg
 1               5                  10                  15

Gly Ser His Met Thr Lys Lys Ala Ala Val Ser Glu Leu Leu Gln Ala
                 20                  25                  30

Ser Ala Pro Tyr Lys Ala Asp Val Glu Leu Cys Arg Ser Asp Tyr Lys
```

```
                35                  40                  45
Leu Tyr Asn Lys Asn Ser Ser Leu Lys Asn Leu Gly Glu Cys Thr
    50                  55                  60

Gly Gly Lys Asn Gly Ile Ala Ala Asp Ile Thr Thr Ala Lys Gly Tyr
65                  70                  75                  80

Val Lys Ser Val Thr Thr Ser Asn Gly Ala Ile Thr Val Lys Gly Asp
                85                  90                  95

Gly Thr Leu Ala Asn Met Glu Tyr Ile Leu Gln Ala Thr Gly Asn Ala
            100                 105                 110

Ala Thr Gly Val Thr Trp Thr Thr Cys Lys Gly Thr Asp Ala Ser Leu
        115                 120                 125

Phe Pro Ala Asn Phe Cys Gly Ser Val Thr Gln
        130                 135

<210> SEQ ID NO 22
<211> LENGTH: 145
<212> TYPE: PRT
<213> ORGANISM: Artificial sequence
<220> FEATURE:
<223> OTHER INFORMATION: Chimeric Protein

<400> SEQUENCE: 22

Met Gly Ser Ser His His His His Ser Ser Gly Leu Val Pro Arg
1               5                   10                  15

Gly Ser His Met Thr Lys Lys Ala Ala Val Ser Glu Leu Leu Gln Ala
                20                  25                  30

Ser Ala Pro Tyr Lys Ala Asp Val Glu Leu Cys Leu Val Arg Ser Asp
            35                  40                  45

Tyr Lys Leu Tyr Asn Lys Asn Ser Ser Ser Thr Leu Lys Asn Leu Gly
        50                  55                  60

Glu Arg His Thr Cys Thr Gly Gly Lys Asn Gly Ile Ala Ala Asp Ile
65                  70                  75                  80

Thr Thr Ala Lys Gly Tyr Val Lys Ser Val Thr Thr Ser Asn Gly Ala
                85                  90                  95

Ile Thr Val Lys Gly Asp Gly Thr Leu Ala Asn Met Glu Tyr Ile Leu
            100                 105                 110

Gln Ala Thr Gly Asn Ala Ala Thr Gly Val Thr Trp Thr Thr Cys Lys
        115                 120                 125

Gly Thr Asp Ala Ser Leu Phe Pro Ala Asn Phe Cys Gly Ser Val Thr
    130                 135                 140

Gln
145

<210> SEQ ID NO 23
<211> LENGTH: 136
<212> TYPE: PRT
<213> ORGANISM: Artificial sequence
<220> FEATURE:
<223> OTHER INFORMATION: Chimeric Protein

<400> SEQUENCE: 23

Met Gly Ser Ser His His His His Ser Ser Gly Leu Val Pro Arg
1               5                   10                  15

Gly Ser His Met Thr Lys Lys Ala Ala Val Ser Glu Leu Leu Gln Ala
                20                  25                  30

Ser Ala Pro Tyr Lys Ala Asp Val Glu Leu Cys Val Thr Ser Thr Asn
            35                  40                  45

Glu Thr Thr Asn Cys Thr Gly Gly Lys Asn Gly Ile Ala Ala Asp Ile
```

```
                    50                  55                  60
Thr Thr Ala Lys Gly Tyr Val Lys Ser Val Thr Thr Ser Asn Gly Ala
 65                  70                  75                  80

Ile Thr Val Lys Gly Asp Gly Thr Leu Ala Asn Met Glu Tyr Ile Leu
                     85                  90                  95

Gln Ala Thr Gly Asn Ala Ala Thr Gly Val Thr Trp Thr Thr Cys Arg
                    100                 105                 110

Ser Asp Tyr Lys Leu Tyr Asn Lys Asn Ser Ser Thr Leu Lys Asn Leu
                115                 120                 125

Gly Glu Cys Gly Ser Val Thr Gln
            130                 135

<210> SEQ ID NO 24
<211> LENGTH: 141
<212> TYPE: PRT
<213> ORGANISM: Artificial sequence
<220> FEATURE:
<223> OTHER INFORMATION: Chimeric Protein

<400> SEQUENCE: 24

Met Gly Ser Ser His His His His Ser Ser Gly Leu Val Pro Arg
 1               5                  10                  15

Gly Ser His Met Thr Lys Lys Ala Ala Val Ser Glu Leu Leu Gln Ala
                20                  25                  30

Ser Ala Pro Tyr Lys Ala Asp Val Glu Leu Cys Val Thr Ser Thr Asn
            35                  40                  45

Glu Thr Thr Asn Cys Thr Gly Gly Lys Asn Gly Ile Ala Ala Asp Ile
         50                  55                  60

Thr Thr Ala Lys Gly Tyr Val Lys Ser Val Thr Thr Ser Asn Gly Ala
 65                  70                  75                  80

Ile Thr Val Lys Gly Asp Gly Thr Leu Ala Asn Met Glu Tyr Ile Leu
                     85                  90                  95

Gln Ala Thr Gly Asn Ala Ala Thr Gly Val Thr Trp Thr Thr Cys Leu
                    100                 105                 110

Val Arg Ser Asp Tyr Lys Leu Tyr Asn Lys Asn Ser Ser Thr Leu Lys
                115                 120                 125

Asn Leu Gly Glu Arg His Thr Cys Gly Ser Val Thr Gln
            130                 135                 140

<210> SEQ ID NO 25
<211> LENGTH: 148
<212> TYPE: PRT
<213> ORGANISM: Artificial sequence
<220> FEATURE:
<223> OTHER INFORMATION: Chimeric Protein

<400> SEQUENCE: 25

Met Gly Ser Ser His His His His Ser Ser Gly Leu Val Pro Arg
 1               5                  10                  15

Gly Ser His Met Thr Lys Lys Ala Ala Val Ser Glu Leu Leu Gln Ala
                20                  25                  30

Ser Ala Pro Tyr Lys Ala Asp Val Glu Leu Cys Val Thr Ser Thr Asn
            35                  40                  45

Glu Thr Thr Asn Cys Thr Gly Gly Lys Asn Gly Ile Ala Ala Asp Ile
         50                  55                  60

Thr Thr Ala Lys Gly Tyr Val Lys Ser Val Thr Thr Ser Asn Gly Ala
 65                  70                  75                  80

Ile Thr Val Lys Gly Asp Gly Thr Leu Ala Asn Met Glu Tyr Ile Leu
```

```
                    85                  90                  95
Gln Ala Thr Gly Asn Ala Ala Thr Gly Val Thr Trp Thr Thr Cys Lys
            100                 105                 110
Gly Thr Asp Ala Ser Leu Phe Pro Ala Asn Phe Cys Gly Ser Val Thr
            115                 120                 125
Gln Arg Ser Asp Tyr Lys Leu Tyr Asn Lys Asn Ser Ser Thr Leu Lys
            130                 135                 140
Asn Leu Gly Glu
145

<210> SEQ ID NO 26
<211> LENGTH: 153
<212> TYPE: PRT
<213> ORGANISM: Artificial sequence
<220> FEATURE:
<223> OTHER INFORMATION: Chimeric Protein

<400> SEQUENCE: 26

Met Gly Ser Ser His His His His Ser Gly Leu Val Pro Arg
1               5                   10                  15
Gly Ser His Met Thr Lys Lys Ala Ala Val Ser Glu Leu Leu Gln Ala
            20                  25                  30
Ser Ala Pro Tyr Lys Ala Asp Val Glu Leu Cys Val Thr Ser Thr Asn
            35                  40                  45
Glu Thr Thr Asn Cys Thr Gly Gly Lys Asn Gly Ile Ala Ala Asp Ile
        50                  55                  60
Thr Thr Ala Lys Gly Tyr Val Lys Ser Val Thr Thr Ser Asn Gly Ala
65                  70                  75                  80
Ile Thr Val Lys Gly Asp Gly Thr Leu Ala Asn Met Glu Tyr Ile Leu
                85                  90                  95
Gln Ala Thr Gly Asn Ala Ala Thr Gly Val Thr Trp Thr Thr Cys Lys
            100                 105                 110
Gly Thr Asp Ala Ser Leu Phe Pro Ala Asn Phe Cys Gly Ser Val Thr
            115                 120                 125
Gln Leu Val Arg Ser Asp Tyr Lys Leu Tyr Asn Lys Asn Ser Ser Thr
            130                 135                 140
Leu Lys Asn Leu Gly Glu Arg His Thr
145                 150

<210> SEQ ID NO 27
<211> LENGTH: 133
<212> TYPE: PRT
<213> ORGANISM: Artificial sequence
<220> FEATURE:
<223> OTHER INFORMATION: Chimeric Protein

<400> SEQUENCE: 27

Met Gly Ser Ser His His His His Ser Ser Gly Leu Val Pro Arg
1               5                   10                  15
Gly Ser His Met Thr Lys Lys Ala Ala Val Ser Glu Leu Leu Gln Ala
            20                  25                  30
Ser Ala Pro Tyr Lys Ala Asp Val Glu Leu Cys Arg Ser Asp Tyr Lys
            35                  40                  45
Phe Tyr Asp Asn Lys Arg Ile Asp Cys Thr Gly Gly Lys Asn Gly Ile
        50                  55                  60
Ala Ala Asp Ile Thr Thr Ala Lys Gly Tyr Val Lys Ser Val Thr Thr
65                  70                  75                  80
Ser Asn Gly Ala Ile Thr Val Lys Gly Asp Gly Thr Leu Ala Asn Met
```

```
                        85                  90                  95
Glu Tyr Ile Leu Gln Ala Thr Gly Asn Ala Ala Thr Gly Val Thr Trp
                100                 105                 110

Thr Thr Cys Lys Gly Thr Asp Ala Ser Leu Phe Pro Ala Asn Phe Cys
            115                 120                 125

Gly Ser Val Thr Gln
        130

<210> SEQ ID NO 28
<211> LENGTH: 138
<212> TYPE: PRT
<213> ORGANISM: Artificial sequence
<220> FEATURE:
<223> OTHER INFORMATION: Chimeric Protein

<400> SEQUENCE: 28

Met Gly Ser Ser His His His His His Ser Ser Gly Leu Val Pro Arg
1               5                   10                  15

Gly Ser His Met Thr Lys Lys Ala Ala Val Ser Glu Leu Leu Gln Ala
                20                  25                  30

Ser Ala Pro Tyr Lys Ala Asp Val Glu Leu Cys Leu Val Arg Ser Asp
            35                  40                  45

Tyr Lys Phe Tyr Asp Asn Lys Arg Ile Asp Arg His Thr Cys Thr Gly
        50                  55                  60

Gly Lys Asn Gly Ile Ala Ala Asp Ile Thr Thr Ala Lys Gly Tyr Val
65                  70                  75                  80

Lys Ser Val Thr Thr Ser Asn Gly Ala Ile Thr Val Lys Gly Asp Gly
                85                  90                  95

Thr Leu Ala Asn Met Glu Tyr Ile Leu Gln Ala Thr Gly Asn Ala Ala
            100                 105                 110

Thr Gly Val Thr Trp Thr Thr Cys Lys Gly Thr Asp Ala Ser Leu Phe
        115                 120                 125

Pro Ala Asn Phe Cys Gly Ser Val Thr Gln
    130                 135

<210> SEQ ID NO 29
<211> LENGTH: 130
<212> TYPE: PRT
<213> ORGANISM: Artificial sequence
<220> FEATURE:
<223> OTHER INFORMATION: Chimeric Protein

<400> SEQUENCE: 29

Met Gly Ser Ser His His His His His Ser Ser Gly Leu Val Pro Arg
1               5                   10                  15

Gly Ser His Met Thr Lys Lys Ala Ala Val Ser Glu Leu Leu Gln Ala
                20                  25                  30

Ser Ala Pro Tyr Lys Ala Asp Val Glu Leu Cys Val Thr Ser Thr Asn
            35                  40                  45

Glu Thr Thr Asn Cys Thr Gly Gly Lys Asn Gly Ile Ala Ala Asp Ile
        50                  55                  60

Thr Thr Ala Lys Gly Tyr Val Lys Ser Val Thr Ser Asn Gly Ala
65                  70                  75                  80

Ile Thr Val Lys Gly Asp Gly Thr Leu Ala Asn Met Glu Tyr Ile Leu
                85                  90                  95

Gln Ala Thr Gly Asn Ala Ala Thr Gly Val Thr Trp Thr Thr Cys Arg
            100                 105                 110

Ser Asp Tyr Lys Phe Tyr Asp Asn Lys Arg Ile Asp Cys Gly Ser Val
```

```
                  115                 120                 125

Thr Gln
    130

<210> SEQ ID NO 30
<211> LENGTH: 135
<212> TYPE: PRT
<213> ORGANISM: Artificial sequence
<220> FEATURE:
<223> OTHER INFORMATION: Chimeric Protein

<400> SEQUENCE: 30

Met Gly Ser Ser His His His His His Ser Gly Leu Val Pro Arg
1               5                   10                  15

Gly Ser His Met Thr Lys Lys Ala Ala Val Ser Glu Leu Leu Gln Ala
            20                  25                  30

Ser Ala Pro Tyr Lys Ala Asp Val Glu Leu Cys Val Thr Ser Thr Asn
            35                  40                  45

Glu Thr Thr Asn Cys Thr Gly Gly Lys Asn Gly Ile Ala Ala Asp Ile
    50                  55                  60

Thr Thr Ala Lys Gly Tyr Val Lys Ser Val Thr Thr Ser Asn Gly Ala
65                  70                  75                  80

Ile Thr Val Lys Gly Asp Gly Thr Leu Ala Asn Met Glu Tyr Ile Leu
                85                  90                  95

Gln Ala Thr Gly Asn Ala Ala Thr Gly Val Thr Trp Thr Thr Cys Leu
            100                 105                 110

Val Arg Ser Asp Tyr Lys Phe Tyr Asp Asn Lys Arg Ile Asp Arg His
            115                 120                 125

Thr Cys Gly Ser Val Thr Gln
    130                 135

<210> SEQ ID NO 31
<211> LENGTH: 142
<212> TYPE: PRT
<213> ORGANISM: Artificial sequence
<220> FEATURE:
<223> OTHER INFORMATION: Chimeric Protein

<400> SEQUENCE: 31

Met Gly Ser Ser His His His His His Ser Gly Leu Val Pro Arg
1               5                   10                  15

Gly Ser His Met Thr Lys Lys Ala Ala Val Ser Glu Leu Leu Gln Ala
            20                  25                  30

Ser Ala Pro Tyr Lys Ala Asp Val Glu Leu Cys Val Thr Ser Thr Asn
            35                  40                  45

Glu Thr Thr Asn Cys Thr Gly Gly Lys Asn Gly Ile Ala Ala Asp Ile
    50                  55                  60

Thr Thr Ala Lys Gly Tyr Val Lys Ser Val Thr Thr Ser Asn Gly Ala
65                  70                  75                  80

Ile Thr Val Lys Gly Asp Gly Thr Leu Ala Asn Met Glu Tyr Ile Leu
                85                  90                  95

Gln Ala Thr Gly Asn Ala Ala Thr Gly Val Thr Trp Thr Thr Cys Lys
            100                 105                 110

Gly Thr Asp Ala Ser Leu Phe Pro Ala Asn Phe Cys Gly Ser Val Thr
            115                 120                 125

Gln Arg Ser Asp Tyr Lys Phe Tyr Asp Asn Lys Arg Ile Asp
    130                 135                 140
```

<210> SEQ ID NO 32
<211> LENGTH: 147
<212> TYPE: PRT
<213> ORGANISM: Artificial sequence
<220> FEATURE:
<223> OTHER INFORMATION: Chimeric Protein

<400> SEQUENCE: 32

```
Met Gly Ser Ser His His His His His Ser Ser Gly Leu Val Pro Arg
 1               5                  10                  15

Gly Ser His Met Thr Lys Lys Ala Ala Val Ser Glu Leu Leu Gln Ala
            20                  25                  30

Ser Ala Pro Tyr Lys Ala Asp Val Glu Leu Cys Val Thr Ser Thr Asn
        35                  40                  45

Glu Thr Thr Asn Cys Thr Gly Gly Lys Asn Gly Ile Ala Ala Asp Ile
    50                  55                  60

Thr Thr Ala Lys Gly Tyr Val Lys Ser Val Thr Thr Ser Asn Gly Ala
65                  70                  75                  80

Ile Thr Val Lys Gly Asp Gly Thr Leu Ala Asn Met Glu Tyr Ile Leu
                85                  90                  95

Gln Ala Thr Gly Asn Ala Ala Thr Gly Val Thr Trp Thr Thr Cys Lys
            100                 105                 110

Gly Thr Asp Ala Ser Leu Phe Pro Ala Asn Phe Cys Gly Ser Val Thr
        115                 120                 125

Gln Leu Val Arg Ser Asp Tyr Lys Phe Tyr Asp Asn Lys Arg Ile Asp
    130                 135                 140

Arg His Thr
145
```

<210> SEQ ID NO 33
<211> LENGTH: 447
<212> TYPE: DNA
<213> ORGANISM: H. influenzae
<220> FEATURE:
<221> NAME/KEY: CDS
<222> LOCATION: (1)..(447)

<400> SEQUENCE: 33

```
atg aaa tta aca aca cag caa acc ttg aaa aaa ggg ttt aca tta ata       48
Met Lys Leu Thr Thr Gln Gln Thr Leu Lys Lys Gly Phe Thr Leu Ile
 1               5                  10                  15 gag cta atg att gtg att gca att att gct att tta gcc act atc gca       96
Glu Leu Met Ile Val Ile Ala Ile Ile Ala Ile Leu Ala Thr Ile Ala
            20                  25                  30 att ccc tct tat caa aat tat act aaa aaa gca gcg gta tct gaa tta      144
Ile Pro Ser Tyr Gln Asn Tyr Thr Lys Lys Ala Ala Val Ser Glu Leu
        35                  40                  45 ctg caa gcg tca gcg cct tat aag gct gat gtg gaa tta tgt gta tat      192
Leu Gln Ala Ser Ala Pro Tyr Lys Ala Asp Val Glu Leu Cys Val Tyr
    50                  55                  60 agc aca aat gaa aca aca aac tgt acg ggt gga aaa aat ggt att gca      240
Ser Thr Asn Glu Thr Thr Asn Cys Thr Gly Gly Lys Asn Gly Ile Ala
65                  70                  75                  80 gca gat ata acc aca gca aaa ggc tat gta aaa tca gtg aca aca agc      288
Ala Asp Ile Thr Thr Ala Lys Gly Tyr Val Lys Ser Val Thr Thr Ser
                85                  90                  95 aac ggt gca ata aca gta aaa ggg gat ggc aca ttg gca aat atg gaa      336
Asn Gly Ala Ile Thr Val Lys Gly Asp Gly Thr Leu Ala Asn Met Glu
            100                 105                 110 tat att ttg caa gct aca ggt aat gct gca aca ggt gta act tgg aca      384
Tyr Ile Leu Gln Ala Thr Gly Asn Ala Ala Thr Gly Val Thr Trp Thr
```

```
aca act tgc aaa gga acg gat gcc tct tta ttt cca gca aat ttt tgc      432
Thr Thr Cys Lys Gly Thr Asp Ala Ser Leu Phe Pro Ala Asn Phe Cys
        130                 135                 140 gga agt gtc aca caa                                                  447
Gly Ser Val Thr Gln
145

<210> SEQ ID NO 34
<211> LENGTH: 149
<212> TYPE: PRT
<213> ORGANISM: H. influenzae

<400> SEQUENCE: 34

Met Lys Leu Thr Thr Gln Gln Thr Leu Lys Lys Gly Phe Thr Leu Ile
1               5                   10                  15

Glu Leu Met Ile Val Ile Ala Ile Ile Ala Ile Leu Ala Thr Ile Ala
            20                  25                  30

Ile Pro Ser Tyr Gln Asn Tyr Thr Lys Lys Ala Ala Val Ser Glu Leu
        35                  40                  45

Leu Gln Ala Ser Ala Pro Tyr Lys Ala Asp Val Glu Leu Cys Val Tyr
    50                  55                  60

Ser Thr Asn Glu Thr Thr Asn Cys Thr Gly Gly Lys Asn Gly Ile Ala
65                  70                  75                  80

Ala Asp Ile Thr Thr Ala Lys Gly Tyr Val Lys Ser Val Thr Thr Ser
                85                  90                  95

Asn Gly Ala Ile Thr Val Lys Gly Asp Gly Thr Leu Ala Asn Met Glu
            100                 105                 110

Tyr Ile Leu Gln Ala Thr Gly Asn Ala Ala Thr Gly Val Thr Trp Thr
        115                 120                 125

Thr Thr Cys Lys Gly Thr Asp Ala Ser Leu Phe Pro Ala Asn Phe Cys
    130                 135                 140

Gly Ser Val Thr Gln
145

<210> SEQ ID NO 35
<211> LENGTH: 447
<212> TYPE: DNA
<213> ORGANISM: H. influenzae
<220> FEATURE:
<221> NAME/KEY: CDS
<222> LOCATION: (1)..(447)

<400> SEQUENCE: 35 atg aaa tta aca aca cag caa acc ttg aaa aaa ggg ttt aca tta ata       48
Met Lys Leu Thr Thr Gln Gln Thr Leu Lys Lys Gly Phe Thr Leu Ile
1               5                   10                  15 gag cta atg att gtg att gca att att gct att tta gcc act atc gca       96
Glu Leu Met Ile Val Ile Ala Ile Ile Ala Ile Leu Ala Thr Ile Ala
            20                  25                  30 att ccc tct tat caa aat tat act aaa aaa gca gcg gta tct gaa tta      144
Ile Pro Ser Tyr Gln Asn Tyr Thr Lys Lys Ala Ala Val Ser Glu Leu
        35                  40                  45 ctg caa gcg tca gcg cct tat aag gct gat gtg gaa tta tgt gta tat      192
Leu Gln Ala Ser Ala Pro Tyr Lys Ala Asp Val Glu Leu Cys Val Tyr
    50                  55                  60 agc aca aat gaa aca aca aac tgt acg ggt gga aaa aat ggt att gca      240
Ser Thr Asn Glu Thr Thr Asn Cys Thr Gly Gly Lys Asn Gly Ile Ala
65                  70                  75                  80 gca gat ata acc aca gca aaa ggc tat gta aaa tca gtg aca aca agc      288
```

```
                                       -continued
Ala Asp Ile Thr Thr Ala Lys Gly Tyr Val Lys Ser Val Thr Thr Ser
             85                  90                  95 aac ggt gca ata aca gta aaa ggg gat ggc aca ttg gca aat atg gaa   336
Asn Gly Ala Ile Thr Val Lys Gly Asp Gly Thr Leu Ala Asn Met Glu
            100                 105                 110 tat att ttg caa gct aca ggt aat gct gca aca ggt gta act tgg aca   384
Tyr Ile Leu Gln Ala Thr Gly Asn Ala Ala Thr Gly Val Thr Trp Thr
        115                 120                 125 aca act tgc aaa gga acg gat gcc tct tta ttt cca gca aat ttt tgc   432
Thr Thr Cys Lys Gly Thr Asp Ala Ser Leu Phe Pro Ala Asn Phe Cys
    130                 135                 140 gga agt gtc aca caa                                               447
Gly Ser Val Thr Gln
145

<210> SEQ ID NO 36
<211> LENGTH: 149
<212> TYPE: PRT
<213> ORGANISM: H. influenzae

<400> SEQUENCE: 36

Met Lys Leu Thr Thr Gln Gln Thr Leu Lys Lys Gly Phe Thr Leu Ile
1               5                   10                  15

Glu Leu Met Ile Val Ile Ala Ile Ile Ala Ile Leu Ala Thr Ile Ala
            20                  25                  30

Ile Pro Ser Tyr Gln Asn Tyr Thr Lys Lys Ala Ala Val Ser Glu Leu
        35                  40                  45

Leu Gln Ala Ser Ala Pro Tyr Lys Ala Asp Val Glu Leu Cys Val Tyr
    50                  55                  60

Ser Thr Asn Glu Thr Thr Asn Cys Thr Gly Gly Lys Asn Gly Ile Ala
65                  70                  75                  80

Ala Asp Ile Thr Thr Ala Lys Gly Tyr Val Lys Ser Val Thr Thr Ser
                85                  90                  95

Asn Gly Ala Ile Thr Val Lys Gly Asp Gly Thr Leu Ala Asn Met Glu
            100                 105                 110

Tyr Ile Leu Gln Ala Thr Gly Asn Ala Ala Thr Gly Val Thr Trp Thr
        115                 120                 125

Thr Thr Cys Lys Gly Thr Asp Ala Ser Leu Phe Pro Ala Asn Phe Cys
    130                 135                 140

Gly Ser Val Thr Gln
145

<210> SEQ ID NO 37
<211> LENGTH: 447
<212> TYPE: DNA
<213> ORGANISM: H. influenzae
<220> FEATURE:
<221> NAME/KEY: CDS
<222> LOCATION: (1)..(447)

<400> SEQUENCE: 37 atg aaa tta aca aca cag caa acc ttg aaa aaa ggg ttt aca tta ata    48
Met Lys Leu Thr Thr Gln Gln Thr Leu Lys Lys Gly Phe Thr Leu Ile
1               5                   10                  15 gag cta atg att gtg att gca att att gct att tta gcc act atc gca    96
Glu Leu Met Ile Val Ile Ala Ile Ile Ala Ile Leu Ala Thr Ile Ala
            20                  25                  30 att ccc tct tat caa aat tat act aaa aaa gca gcg tta tct gaa tta   144
Ile Pro Ser Tyr Gln Asn Tyr Thr Lys Lys Ala Ala Val Ser Glu Leu
        35                  40                  45
```

```
ctg caa gcg tca gcg cct tat aag gct gat gtg gaa tta tgt gta tat       192
Leu Gln Ala Ser Ala Pro Tyr Lys Ala Asp Val Glu Leu Cys Val Tyr
    50                  55                  60 agc aca aat gaa aca aca aac tgt acg ggt gga aaa aat ggt att gca       240
Ser Thr Asn Glu Thr Thr Asn Cys Thr Gly Gly Lys Asn Gly Ile Ala
 65                 70                  75                  80 gca gat ata acc aca gca aaa ggc tat gta aaa tca gtg aca aca agc       288
Ala Asp Ile Thr Thr Ala Lys Gly Tyr Val Lys Ser Val Thr Thr Ser
                85                  90                  95 aac ggt gca ata aca gta aaa ggg gat ggc aca ttg gca aat atg gaa       336
Asn Gly Ala Ile Thr Val Lys Gly Asp Gly Thr Leu Ala Asn Met Glu
            100                 105                 110 tat att ttg caa gct aca ggt aat gct gca aca ggt gta act tgg aca       384
Tyr Ile Leu Gln Ala Thr Gly Asn Ala Ala Thr Gly Val Thr Trp Thr
                115                 120                 125 aca act tgc aaa gga acg gat gcc tct tta ttt cca gca aat ttt tgc       432
Thr Thr Cys Lys Gly Thr Asp Ala Ser Leu Phe Pro Ala Asn Phe Cys
        130                 135                 140 gga agt gtc aca caa                                                   447
Gly Ser Val Thr Gln
145

<210> SEQ ID NO 38
<211> LENGTH: 149
<212> TYPE: PRT
<213> ORGANISM: H. influenzae

<400> SEQUENCE: 38

Met Lys Leu Thr Thr Gln Gln Thr Leu Lys Lys Gly Phe Thr Leu Ile
 1               5                  10                  15

Glu Leu Met Ile Val Ile Ala Ile Ile Ala Ile Leu Ala Thr Ile Ala
            20                  25                  30

Ile Pro Ser Tyr Gln Asn Tyr Thr Lys Lys Ala Ala Val Ser Glu Leu
        35                  40                  45

Leu Gln Ala Ser Ala Pro Tyr Lys Ala Asp Val Glu Leu Cys Val Tyr
    50                  55                  60

Ser Thr Asn Glu Thr Thr Asn Cys Thr Gly Gly Lys Asn Gly Ile Ala
 65                 70                  75                  80

Ala Asp Ile Thr Thr Ala Lys Gly Tyr Val Lys Ser Val Thr Thr Ser
                85                  90                  95

Asn Gly Ala Ile Thr Val Lys Gly Asp Gly Thr Leu Ala Asn Met Glu
            100                 105                 110

Tyr Ile Leu Gln Ala Thr Gly Asn Ala Ala Thr Gly Val Thr Trp Thr
        115                 120                 125

Thr Thr Cys Lys Gly Thr Asp Ala Ser Leu Phe Pro Ala Asn Phe Cys
    130                 135                 140

Gly Ser Val Thr Gln
145

<210> SEQ ID NO 39
<211> LENGTH: 447
<212> TYPE: DNA
<213> ORGANISM: H. influenzae
<220> FEATURE:
<221> NAME/KEY: CDS
<222> LOCATION: (1)..(447)

<400> SEQUENCE: 39 atg aaa tta aca aca cag caa acc ttg aaa aaa ggg ttt aca tta ata        48
Met Lys Leu Thr Thr Gln Gln Thr Leu Lys Lys Gly Phe Thr Leu Ile
 1               5                  10                  15
```

```
gag cta atg att gtg att gca att att gct att tta gcc act atc gca      96
Glu Leu Met Ile Val Ile Ala Ile Ile Ala Ile Leu Ala Thr Ile Ala
            20                  25                  30 att ccc tct tat caa aat tat act aaa aaa gca gcg gta tct gaa tta     144
Ile Pro Ser Tyr Gln Asn Tyr Thr Lys Lys Ala Ala Val Ser Glu Leu
        35                  40                  45 ctg caa gcg tca gcg cct tat aag gct gat gtg gaa tta tgt gta tat    192
Leu Gln Ala Ser Ala Pro Tyr Lys Ala Asp Val Glu Leu Cys Val Tyr
50                  55                  60 agc aca aat gaa aca aca aac tgt acg ggt gga aaa aat ggt att gca    240
Ser Thr Asn Glu Thr Thr Asn Cys Thr Gly Gly Lys Asn Gly Ile Ala
65                  70                  75                  80 gca gat ata acc aca gca aaa ggc tat gta aaa tca gtg aca aca agc    288
Ala Asp Ile Thr Thr Ala Lys Gly Tyr Val Lys Ser Val Thr Thr Ser
                85                  90                  95 aac ggt gca ata aca gta aaa ggg gat ggc aca ttg gca aat atg gaa    336
Asn Gly Ala Ile Thr Val Lys Gly Asp Gly Thr Leu Ala Asn Met Glu
            100                 105                 110 tat att ttg caa gct aca ggt aat gct gca aca ggt gta act tgg aca    384
Tyr Ile Leu Gln Ala Thr Gly Asn Ala Ala Thr Gly Val Thr Trp Thr
        115                 120                 125 aca act tgc aaa gga acg gat gcc tct tta ttt cca gca aat ttt tgc    432
Thr Thr Cys Lys Gly Thr Asp Ala Ser Leu Phe Pro Ala Asn Phe Cys
130                 135                 140 gga agt gtc aca caa                                                 447
Gly Ser Val Thr Gln
145
```

<210> SEQ ID NO 40
<211> LENGTH: 149
<212> TYPE: PRT
<213> ORGANISM: H. influenzae

<400> SEQUENCE: 40

```
Met Lys Leu Thr Thr Gln Gln Thr Leu Lys Lys Gly Phe Thr Leu Ile
1               5                   10                  15

Glu Leu Met Ile Val Ile Ala Ile Ile Ala Ile Leu Ala Thr Ile Ala
            20                  25                  30

Ile Pro Ser Tyr Gln Asn Tyr Thr Lys Lys Ala Ala Val Ser Glu Leu
        35                  40                  45

Leu Gln Ala Ser Ala Pro Tyr Lys Ala Asp Val Glu Leu Cys Val Tyr
    50                  55                  60

Ser Thr Asn Glu Thr Thr Asn Cys Thr Gly Gly Lys Asn Gly Ile Ala
65                  70                  75                  80

Ala Asp Ile Thr Thr Ala Lys Gly Tyr Val Lys Ser Val Thr Thr Ser
                85                  90                  95

Asn Gly Ala Ile Thr Val Lys Gly Asp Gly Thr Leu Ala Asn Met Glu
            100                 105                 110

Tyr Ile Leu Gln Ala Thr Gly Asn Ala Ala Thr Gly Val Thr Trp Thr
        115                 120                 125

Thr Thr Cys Lys Gly Thr Asp Ala Ser Leu Phe Pro Ala Asn Phe Cys
    130                 135                 140

Gly Ser Val Thr Gln
145
```

<210> SEQ ID NO 41
<211> LENGTH: 447
<212> TYPE: DNA
<213> ORGANISM: H. influenzae

```
<220> FEATURE:
<221> NAME/KEY: CDS
<222> LOCATION: (1)..(447)

<400> SEQUENCE: 41 atg aaa tta aca aca cag caa acc ttg aaa aaa ggt ttt aca tta atc        48
Met Lys Leu Thr Thr Gln Gln Thr Leu Lys Lys Gly Phe Thr Leu Ile
1               5                   10                  15 gag cta atg att gtg att gca att att gct att tta gcc act atc gca        96
Glu Leu Met Ile Val Ile Ala Ile Ile Ala Ile Leu Ala Thr Ile Ala
            20                  25                  30 att cct tct tat caa aat tat acc aaa aaa gct tcg gta tcc gaa tta       144
Ile Pro Ser Tyr Gln Asn Tyr Thr Lys Lys Ala Ser Val Ser Glu Leu
        35                  40                  45 ctg caa gca tct gca cct tat aag gct gat gtg gaa tta tgt gta tat       192
Leu Gln Ala Ser Ala Pro Tyr Lys Ala Asp Val Glu Leu Cys Val Tyr
    50                  55                  60 agc aca aat gaa aca aca aac tgt acg ggt gga aaa aat ggt att gca       240
Ser Thr Asn Glu Thr Thr Asn Cys Thr Gly Gly Lys Asn Gly Ile Ala
65                  70                  75                  80 gct gat att aca aca gca aaa ggc tat gta gcc tca gtg aaa act caa       288
Ala Asp Ile Thr Thr Ala Lys Gly Tyr Val Ala Ser Val Lys Thr Gln
                85                  90                  95 tcg ggt ggc att aca gta aaa ggg aat ggc aca ttg gca aat atg gaa       336
Ser Gly Gly Ile Thr Val Lys Gly Asn Gly Thr Leu Ala Asn Met Glu
            100                 105                 110 tat att ttg caa gct aaa ggt aat gct aca gca ggt gta act tgg aca       384
Tyr Ile Leu Gln Ala Lys Gly Asn Ala Thr Ala Gly Val Thr Trp Thr
        115                 120                 125 aca acc tgc aaa gga acg gat gcc tct tta ttt cca gca aat ttt tgc       432
Thr Thr Cys Lys Gly Thr Asp Ala Ser Leu Phe Pro Ala Asn Phe Cys
    130                 135                 140 aga agt gtc aca aaa                                                   447
Arg Ser Val Thr Lys
145

<210> SEQ ID NO 42
<211> LENGTH: 149
<212> TYPE: PRT
<213> ORGANISM: H. influenzae

<400> SEQUENCE: 42

Met Lys Leu Thr Thr Gln Gln Thr Leu Lys Lys Gly Phe Thr Leu Ile
1               5                   10                  15

Glu Leu Met Ile Val Ile Ala Ile Ile Ala Ile Leu Ala Thr Ile Ala
            20                  25                  30

Ile Pro Ser Tyr Gln Asn Tyr Thr Lys Lys Ala Ser Val Ser Glu Leu
        35                  40                  45

Leu Gln Ala Ser Ala Pro Tyr Lys Ala Asp Val Glu Leu Cys Val Tyr
    50                  55                  60

Ser Thr Asn Glu Thr Thr Asn Cys Thr Gly Gly Lys Asn Gly Ile Ala
65                  70                  75                  80

Ala Asp Ile Thr Thr Ala Lys Gly Tyr Val Ala Ser Val Lys Thr Gln
                85                  90                  95

Ser Gly Gly Ile Thr Val Lys Gly Asn Gly Thr Leu Ala Asn Met Glu
            100                 105                 110

Tyr Ile Leu Gln Ala Lys Gly Asn Ala Thr Ala Gly Val Thr Trp Thr
        115                 120                 125

Thr Thr Cys Lys Gly Thr Asp Ala Ser Leu Phe Pro Ala Asn Phe Cys
    130                 135                 140
```

Arg Ser Val Thr Lys
145

<210> SEQ ID NO 43
<211> LENGTH: 447
<212> TYPE: DNA
<213> ORGANISM: H. influenzae
<220> FEATURE:
<221> NAME/KEY: CDS
<222> LOCATION: (1)..(447)

<400> SEQUENCE: 43

```
atg aaa tta aca aca cag caa acc ttg aaa aaa ggg ttt aca tta ata      48
Met Lys Leu Thr Thr Gln Gln Thr Leu Lys Lys Gly Phe Thr Leu Ile
1               5                   10                  15 gag cta atg att gtg att gca att att gct att tta gcc acc atc gca      96
Glu Leu Met Ile Val Ile Ala Ile Ile Ala Ile Leu Ala Thr Ile Ala
                20                  25                  30 att cct tct tat aaa aat tat act aaa aaa gca gcg gta tct gaa tta     144
Ile Pro Ser Tyr Lys Asn Tyr Thr Lys Lys Ala Ala Val Ser Glu Leu
            35                  40                  45 ctg caa gct tct gcg cct tat aag gct gat gtg gaa tta tgt gta tat     192
Leu Gln Ala Ser Ala Pro Tyr Lys Ala Asp Val Glu Leu Cys Val Tyr
        50                  55                  60 agc aca aat gaa ata aca aat tgt atg ggt gga aaa aat ggt att gca     240
Ser Thr Asn Glu Ile Thr Asn Cys Met Gly Gly Lys Asn Gly Ile Ala
65                  70                  75                  80 gct gat att aca aca gca aaa ggc tat gta gcc tca gtg aaa act caa     288
Ala Asp Ile Thr Thr Ala Lys Gly Tyr Val Ala Ser Val Lys Thr Gln
                85                  90                  95 tcg ggt ggc att acc gta aaa ggg gat ggc aca ttg gca aat atg gaa     336
Ser Gly Gly Ile Thr Val Lys Gly Asp Gly Thr Leu Ala Asn Met Glu
            100                 105                 110 tat att ttg caa gct aca ggt aat gct gca gca ggt gta act tgg aca     384
Tyr Ile Leu Gln Ala Thr Gly Asn Ala Ala Ala Gly Val Thr Trp Thr
        115                 120                 125 aca acc tgc aaa gga acg gat gcc tct tta ttt cca gca aat ttt tgc     432
Thr Thr Cys Lys Gly Thr Asp Ala Ser Leu Phe Pro Ala Asn Phe Cys
130                 135                 140 gga agt atc aca caa                                                 447
Gly Ser Ile Thr Gln
145
```

<210> SEQ ID NO 44
<211> LENGTH: 149
<212> TYPE: PRT
<213> ORGANISM: H. influenzae

<400> SEQUENCE: 44

Met Lys Leu Thr Thr Gln Gln Thr Leu Lys Lys Gly Phe Thr Leu Ile
1               5                   10                  15

Glu Leu Met Ile Val Ile Ala Ile Ile Ala Ile Leu Ala Thr Ile Ala
                20                  25                  30

Ile Pro Ser Tyr Lys Asn Tyr Thr Lys Lys Ala Ala Val Ser Glu Leu
            35                  40                  45

Leu Gln Ala Ser Ala Pro Tyr Lys Ala Asp Val Glu Leu Cys Val Tyr
        50                  55                  60

Ser Thr Asn Glu Ile Thr Asn Cys Met Gly Gly Lys Asn Gly Ile Ala
65                  70                  75                  80

Ala Asp Ile Thr Thr Ala Lys Gly Tyr Val Ala Ser Val Lys Thr Gln
                85                  90                  95

```
Ser Gly Gly Ile Thr Val Lys Gly Asp Gly Thr Leu Ala Asn Met Glu
            100                 105                 110

Tyr Ile Leu Gln Ala Thr Gly Asn Ala Ala Ala Gly Val Thr Trp Thr
            115                 120                 125

Thr Thr Cys Lys Gly Thr Asp Ala Ser Leu Phe Pro Ala Asn Phe Cys
        130                 135                 140

Gly Ser Ile Thr Gln
145

<210> SEQ ID NO 45
<211> LENGTH: 447
<212> TYPE: DNA
<213> ORGANISM: H. influenzae
<220> FEATURE:
<221> NAME/KEY: CDS
<222> LOCATION: (1)..(447)

<400> SEQUENCE: 45 atg aaa tta aca aca ctg caa acc ttg aaa aaa ggg ttt aca tta atc        48
Met Lys Leu Thr Thr Leu Gln Thr Leu Lys Lys Gly Phe Thr Leu Ile
1               5                   10                  15 gag cta atg att gtg att gca att att gct att tta gcc act atc gca        96
Glu Leu Met Ile Val Ile Ala Ile Ile Ala Ile Leu Ala Thr Ile Ala
                20                  25                  30 att cct tct tat caa aat tat acc aaa aaa gct gcg gta tcc gaa tta       144
Ile Pro Ser Tyr Gln Asn Tyr Thr Lys Lys Ala Ala Val Ser Glu Leu
            35                  40                  45 ctg caa gct tct gcg cct tat aag gct gat gtg gaa tta tgc gtt tat       192
Leu Gln Ala Ser Ala Pro Tyr Lys Ala Asp Val Glu Leu Cys Val Tyr
        50                  55                  60 agc aca ggc aaa cct tct act tgc tca gga gga agc aat gga att gca       240
Ser Thr Gly Lys Pro Ser Thr Cys Ser Gly Gly Ser Asn Gly Ile Ala
65                  70                  75                  80 gct gat att acg aca gca aaa ggc tat gta gcc tca gtg aaa act caa       288
Ala Asp Ile Thr Thr Ala Lys Gly Tyr Val Ala Ser Val Lys Thr Gln
                85                  90                  95 tca ggt ggt att aca gta aaa ggg aat ggc aca ttg gca aat atg gaa       336
Ser Gly Gly Ile Thr Val Lys Gly Asn Gly Thr Leu Ala Asn Met Glu
            100                 105                 110 tat att ttg caa gct aca ggt aat gct gca aca ggt gta act tgg aca       384
Tyr Ile Leu Gln Ala Thr Gly Asn Ala Ala Thr Gly Val Thr Trp Thr
        115                 120                 125 aca act tgc aaa gga acg gat gcc tct tta ttt cca gca aat ttt tgc       432
Thr Thr Cys Lys Gly Thr Asp Ala Ser Leu Phe Pro Ala Asn Phe Cys
    130                 135                 140 gga agt gtc aca caa                                                   447
Gly Ser Val Thr Gln
145

<210> SEQ ID NO 46
<211> LENGTH: 149
<212> TYPE: PRT
<213> ORGANISM: H. influenzae

<400> SEQUENCE: 46

Met Lys Leu Thr Thr Leu Gln Thr Leu Lys Lys Gly Phe Thr Leu Ile
1               5                   10                  15

Glu Leu Met Ile Val Ile Ala Ile Ile Ala Ile Leu Ala Thr Ile Ala
                20                  25                  30

Ile Pro Ser Tyr Gln Asn Tyr Thr Lys Lys Ala Ala Val Ser Glu Leu
            35                  40                  45
```

```
Leu Gln Ala Ser Ala Pro Tyr Lys Ala Asp Val Glu Leu Cys Val Tyr
     50                  55                  60
Ser Thr Gly Lys Pro Ser Thr Cys Ser Gly Gly Ser Asn Gly Ile Ala
 65                  70                  75                  80
Ala Asp Ile Thr Thr Ala Lys Gly Tyr Val Ala Ser Val Lys Thr Gln
                 85                  90                  95
Ser Gly Gly Ile Thr Val Lys Gly Asn Gly Thr Leu Ala Asn Met Glu
            100                 105                 110
Tyr Ile Leu Gln Ala Thr Gly Asn Ala Ala Thr Gly Val Thr Trp Thr
        115                 120                 125
Thr Thr Cys Lys Gly Thr Asp Ala Ser Leu Phe Pro Ala Asn Phe Cys
130                 135                 140
Gly Ser Val Thr Gln
145
```

```
<210> SEQ ID NO 47
<211> LENGTH: 447
<212> TYPE: DNA
<213> ORGANISM: H. influenzae
<220> FEATURE:
<221> NAME/KEY: CDS
<222> LOCATION: (1)..(447)

<400> SEQUENCE: 47
```

| | | | | | | | | | | | | | | | | |
|---|---|---|---|---|---|---|---|---|---|---|---|---|---|---|---|---|
| atg | aaa | tta | aca | aca | ctg | caa | acc | ttg | aaa | aaa | ggg | ttt | aca | tta | atc | 48 |
| Met | Lys | Leu | Thr | Thr | Leu | Gln | Thr | Leu | Lys | Lys | Gly | Phe | Thr | Leu | Ile | |
| 1 | | | | 5 | | | | | 10 | | | | | 15 | | |
| gag | cta | atg | att | gtg | att | gca | att | att | gct | att | tta | gcc | act | atc | gca | 96 |
| Glu | Leu | Met | Ile | Val | Ile | Ala | Ile | Ile | Ala | Ile | Leu | Ala | Thr | Ile | Ala | |
| | | | | 20 | | | | | 25 | | | | | 30 | | |
| att | cct | tct | tat | caa | aat | tat | acc | aaa | aaa | gct | gcg | gta | tcc | gaa | tta | 144 |
| Ile | Pro | Ser | Tyr | Gln | Asn | Tyr | Thr | Lys | Lys | Ala | Ala | Val | Ser | Glu | Leu | |
| | | | | 35 | | | | | 40 | | | | | 45 | | |
| ctg | caa | gct | tct | gcg | cct | tat | aag | gct | gat | gtg | gaa | tta | tgc | gtt | tat | 192 |
| Leu | Gln | Ala | Ser | Ala | Pro | Tyr | Lys | Ala | Asp | Val | Glu | Leu | Cys | Val | Tyr | |
| | | | | 50 | | | | | 55 | | | | | 60 | | |
| agc | aca | ggc | aaa | ctt | tct | act | tgc | tca | gga | gga | agc | aat | gga | att | gca | 240 |
| Ser | Thr | Gly | Lys | Leu | Ser | Thr | Cys | Ser | Gly | Gly | Ser | Asn | Gly | Ile | Ala | |
| 65 | | | | | 70 | | | | | 75 | | | | | 80 | |
| gct | gat | att | aca | aca | gca | aaa | ggc | tat | gta | gcc | tca | gtg | aaa | act | caa | 288 |
| Ala | Asp | Ile | Thr | Thr | Ala | Lys | Gly | Tyr | Val | Ala | Ser | Val | Lys | Thr | Gln | |
| | | | | 85 | | | | | 90 | | | | | 95 | | |
| tca | ggt | ggt | att | aca | gta | aaa | ggg | aat | ggc | aca | ttg | gca | aat | atg | gaa | 336 |
| Ser | Gly | Gly | Ile | Thr | Val | Lys | Gly | Asn | Gly | Thr | Leu | Ala | Asn | Met | Glu | |
| | | | | 100 | | | | | 105 | | | | | 110 | | |
| tat | att | ttg | caa | gct | aaa | ggt | aat | gct | aca | gca | ggt | gta | act | tgg | aca | 384 |
| Tyr | Ile | Leu | Gln | Ala | Lys | Gly | Asn | Ala | Thr | Ala | Gly | Val | Thr | Trp | Thr | |
| | | | | 115 | | | | | 120 | | | | | 125 | | |
| aca | acc | tgc | aaa | gga | acg | gat | gcc | tct | tta | ttt | cca | gca | aat | ttt | tgc | 432 |
| Thr | Thr | Cys | Lys | Gly | Thr | Asp | Ala | Ser | Leu | Phe | Pro | Ala | Asn | Phe | Cys | |
| 130 | | | | | 135 | | | | | 140 | | | | | | |
| gga | agt | gtc | aca | aaa | | | | | | | | | | | | 447 |
| Gly | Ser | Val | Thr | Lys | | | | | | | | | | | | |
| | | | | 145 | | | | | | | | | | | | |

```
<210> SEQ ID NO 48
<211> LENGTH: 149
<212> TYPE: PRT
<213> ORGANISM: H. influenzae

<400> SEQUENCE: 48
```

```
Met Lys Leu Thr Thr Leu Gln Thr Leu Lys Lys Gly Phe Thr Leu Ile
1               5                   10                  15

Glu Leu Met Ile Val Ile Ala Ile Ile Ala Ile Leu Ala Thr Ile Ala
            20                  25                  30

Ile Pro Ser Tyr Gln Asn Tyr Thr Lys Lys Ala Ala Val Ser Glu Leu
        35                  40                  45

Leu Gln Ala Ser Ala Pro Tyr Lys Ala Asp Val Glu Leu Cys Val Tyr
    50                  55                  60

Ser Thr Gly Lys Leu Ser Thr Cys Ser Gly Gly Ser Asn Gly Ile Ala
65                  70                  75                  80

Ala Asp Ile Thr Thr Ala Lys Gly Tyr Val Ala Ser Val Lys Thr Gln
                85                  90                  95

Ser Gly Gly Ile Thr Val Lys Gly Asn Gly Thr Leu Ala Asn Met Glu
            100                 105                 110

Tyr Ile Leu Gln Ala Lys Gly Asn Ala Thr Ala Gly Val Thr Trp Thr
        115                 120                 125

Thr Thr Cys Lys Gly Thr Asp Ala Ser Leu Phe Pro Ala Asn Phe Cys
    130                 135                 140

Gly Ser Val Thr Lys
145
```

<210> SEQ ID NO 49
<211> LENGTH: 447
<212> TYPE: DNA
<213> ORGANISM: H. influenzae
<220> FEATURE:
<221> NAME/KEY: CDS
<222> LOCATION: (1)..(447)

<400> SEQUENCE: 49

```
atg aaa tta aca aca cag caa acc ttg aaa aaa ggt ttt aca tta atc      48
Met Lys Leu Thr Thr Gln Gln Thr Leu Lys Lys Gly Phe Thr Leu Ile
1               5                   10                  15 gag cta atg att gtg att gca att att gct att tta gcc act atc gca      96
Glu Leu Met Ile Val Ile Ala Ile Ile Ala Ile Leu Ala Thr Ile Ala
            20                  25                  30 att cct tct tat caa aat tat acc aaa aaa gct tcg gta tcc gaa tta     144
Ile Pro Ser Tyr Gln Asn Tyr Thr Lys Lys Ala Ser Val Ser Glu Leu
        35                  40                  45 ctg caa gct tcc gca cct tat aag tca gat gtg gaa tta tgc gtt tat     192
Leu Gln Ala Ser Ala Pro Tyr Lys Ser Asp Val Glu Leu Cys Val Tyr
    50                  55                  60 agc aca ggc aaa cct tct act tgc tca gga gga agc aat gga att gca     240
Ser Thr Gly Lys Pro Ser Thr Cys Ser Gly Gly Ser Asn Gly Ile Ala
65                  70                  75                  80 gct gat att aca aca gca aaa ggc tat gta gcc tca gtg aaa act caa     288
Ala Asp Ile Thr Thr Ala Lys Gly Tyr Val Ala Ser Val Lys Thr Gln
                85                  90                  95 tca ggt ggt att aca gta aaa ggg aat ggc aca ttg gca aat atg gaa     336
Ser Gly Gly Ile Thr Val Lys Gly Asn Gly Thr Leu Ala Asn Met Glu
            100                 105                 110 tat att ttg caa gct aaa ggt aat gct aca gca ggt gta act tgg aca     384
Tyr Ile Leu Gln Ala Lys Gly Asn Ala Thr Ala Gly Val Thr Trp Thr
        115                 120                 125 aca acc tgc aaa gga acg gat gcc tct tta ttt cca gca aat ttt tgc     432
Thr Thr Cys Lys Gly Thr Asp Ala Ser Leu Phe Pro Ala Asn Phe Cys
    130                 135                 140 aga agt gtc aca aaa                                                 447
Arg Ser Val Thr Lys
```

<210> SEQ ID NO 50
<211> LENGTH: 149
<212> TYPE: PRT
<213> ORGANISM: H. influenzae

<400> SEQUENCE: 50

Met Lys Leu Thr Thr Gln Gln Thr Leu Lys Lys Gly Phe Thr Leu Ile
1               5                   10                  15

Glu Leu Met Ile Val Ile Ala Ile Ile Ala Ile Leu Ala Thr Ile Ala
                20                  25                  30

Ile Pro Ser Tyr Gln Asn Tyr Thr Lys Lys Ala Ser Val Ser Glu Leu
            35                  40                  45

Leu Gln Ala Ser Ala Pro Tyr Lys Ser Asp Val Glu Leu Cys Val Tyr
        50                  55                  60

Ser Thr Gly Lys Pro Ser Thr Cys Ser Gly Gly Ser Asn Gly Ile Ala
65                  70                  75                  80

Ala Asp Ile Thr Thr Ala Lys Gly Tyr Val Ala Ser Val Lys Thr Gln
                85                  90                  95

Ser Gly Gly Ile Thr Val Lys Gly Asn Gly Thr Leu Ala Asn Met Glu
            100                 105                 110

Tyr Ile Leu Gln Ala Lys Gly Asn Ala Thr Ala Gly Val Thr Trp Thr
        115                 120                 125

Thr Thr Cys Lys Gly Thr Asp Ala Ser Leu Phe Pro Ala Asn Phe Cys
130                 135                 140

Arg Ser Val Thr Lys
145

<210> SEQ ID NO 51
<211> LENGTH: 447
<212> TYPE: DNA
<213> ORGANISM: H. influenzae
<220> FEATURE:
<221> NAME/KEY: CDS
<222> LOCATION: (1)..(447)

<400> SEQUENCE: 51

```
atg aaa tta aca aca cag caa acc ttg aaa aaa ggg ttt aca tta ata      48
Met Lys Leu Thr Thr Gln Gln Thr Leu Lys Lys Gly Phe Thr Leu Ile
1               5                   10                  15 gag cta atg att gtg att gca att att gct att tta gcc act atc gca      96
Glu Leu Met Ile Val Ile Ala Ile Ile Ala Ile Leu Ala Thr Ile Ala
                20                  25                  30 att ccc tct tat caa aat tat act aaa aaa gcg gcg gta tct gaa tta     144
Ile Pro Ser Tyr Gln Asn Tyr Thr Lys Lys Ala Ala Val Ser Glu Leu
            35                  40                  45 ctg caa gcg tca gcg cct tat aag gct gat gtg gaa tta tgt gta tat     192
Leu Gln Ala Ser Ala Pro Tyr Lys Ala Asp Val Glu Leu Cys Val Tyr
        50                  55                  60 agt aca ggt aaa cct tcc agt tgc tcg gga gga agc aat gga att gcg     240
Ser Thr Gly Lys Pro Ser Ser Cys Ser Gly Gly Ser Asn Gly Ile Ala
65                  70                  75                  80 gct gat att aca aca gca aaa ggc tat gta aaa tca gtg aca aca agc     288
Ala Asp Ile Thr Thr Ala Lys Gly Tyr Val Lys Ser Val Thr Thr Ser
                85                  90                  95 aac ggt gca ata aca gta aaa ggg gat ggc aca ttg gca aat atg gaa     336
Asn Gly Ala Ile Thr Val Lys Gly Asp Gly Thr Leu Ala Asn Met Glu
            100                 105                 110 tat att ttg caa gcc agt ggt aat gct gca aca ggt gta act tgg aca     384
```

```
Tyr Ile Leu Gln Ala Ser Gly Asn Ala Ala Thr Gly Val Thr Trp Thr
            115                 120                 125 aca act tgc aaa gga acg gat gcc tct tta ttt cca gca aat ttt tgc    432
Thr Thr Cys Lys Gly Thr Asp Ala Ser Leu Phe Pro Ala Asn Phe Cys
    130                 135                 140 gga agt gtc aca caa                                                447
Gly Ser Val Thr Gln
145

<210> SEQ ID NO 52
<211> LENGTH: 149
<212> TYPE: PRT
<213> ORGANISM: H. influenzae

<400> SEQUENCE: 52

Met Lys Leu Thr Thr Gln Gln Thr Leu Lys Lys Gly Phe Thr Leu Ile
1               5                   10                  15

Glu Leu Met Ile Val Ile Ala Ile Ala Ile Leu Ala Thr Ile Ala
            20                  25                  30

Ile Pro Ser Tyr Gln Asn Tyr Thr Lys Lys Ala Ala Val Ser Glu Leu
            35                  40                  45

Leu Gln Ala Ser Ala Pro Tyr Lys Ala Asp Val Glu Leu Cys Val Tyr
        50                  55                  60

Ser Thr Gly Lys Pro Ser Ser Cys Ser Gly Gly Ser Asn Gly Ile Ala
65                  70                  75                  80

Ala Asp Ile Thr Thr Ala Lys Gly Tyr Val Lys Ser Val Thr Thr Ser
                85                  90                  95

Asn Gly Ala Ile Thr Val Lys Gly Asp Gly Thr Leu Ala Asn Met Glu
            100                 105                 110

Tyr Ile Leu Gln Ala Ser Gly Asn Ala Ala Thr Gly Val Thr Trp Thr
        115                 120                 125

Thr Thr Cys Lys Gly Thr Asp Ala Ser Leu Phe Pro Ala Asn Phe Cys
    130                 135                 140

Gly Ser Val Thr Gln
145

<210> SEQ ID NO 53
<211> LENGTH: 40
<212> TYPE: PRT
<213> ORGANISM: Artificial sequence
<220> FEATURE:
<223> OTHER INFORMATION: Synthetic Peptide

<400> SEQUENCE: 53

Arg Ser Asp Tyr Lys Phe Tyr Glu Asp Ala Asn Gly Thr Arg Asp His
1               5                   10                  15

Lys Lys Gly Pro Ser Leu Lys Leu Leu Ser Leu Ile Lys Gly Val Ile
            20                  25                  30

Val His Arg Leu Glu Gly Val Glu
        35                  40

<210> SEQ ID NO 54
<211> LENGTH: 129
<212> TYPE: PRT
<213> ORGANISM: Artificial sequence
<220> FEATURE:
<223> OTHER INFORMATION: Chimeric protein

<400> SEQUENCE: 54

Gly Ser His Met Thr Lys Lys Ala Ala Val Ser Glu Leu Leu Gln Ala
1               5                   10                  15
```

Ser Ala Pro Tyr Lys Ala Asp Val Glu Leu Cys Leu Val Arg Ser Asp
            20                  25                  30

Tyr Lys Phe Tyr Glu Asp Ala Asn Gly Thr Arg Asp His Lys Lys Gly
        35                  40                  45

Arg His Thr Cys Thr Gly Gly Lys Asn Gly Ile Ala Ala Asp Ile Thr
    50                  55                  60

Thr Ala Lys Gly Tyr Val Lys Ser Val Thr Thr Ser Asn Gly Ala Ile
65                  70                  75                  80

Thr Val Lys Gly Asp Gly Thr Leu Ala Asn Met Glu Tyr Ile Leu Gln
                85                  90                  95

Ala Thr Gly Asn Ala Ala Thr Gly Val Thr Trp Thr Thr Cys Lys
            100                 105                 110

Gly Thr Asp Ala Ser Leu Phe Pro Ala Asn Phe Cys Gly Ser Val Thr
            115                 120                 125

Gln

<210> SEQ ID NO 55
<211> LENGTH: 126
<212> TYPE: PRT
<213> ORGANISM: Artificial sequence
<220> FEATURE:
<223> OTHER INFORMATION: Chimeric protein

<400> SEQUENCE: 55

Gly Ser His Met Thr Lys Lys Ala Ala Val Ser Glu Leu Leu Gln Ala
1               5                   10                  15

Ser Ala Pro Tyr Lys Ala Asp Val Glu Leu Cys Val Tyr Ser Thr Asn
            20                  25                  30

Glu Thr Thr Asn Cys Thr Gly Gly Lys Asn Gly Ile Ala Ala Asp Ile
        35                  40                  45

Thr Thr Ala Lys Gly Tyr Val Lys Ser Val Thr Thr Ser Asn Gly Ala
    50                  55                  60

Ile Thr Val Lys Gly Asp Gly Thr Leu Ala Asn Met Glu Tyr Ile Leu
65                  70                  75                  80

Gln Ala Thr Gly Asn Ala Ala Thr Gly Val Thr Trp Thr Thr Thr Cys
                85                  90                  95

Leu Val Arg Ser Asp Tyr Lys Phe Tyr Glu Asp Ala Asn Gly Thr Arg
            100                 105                 110

Asp His Lys Lys Gly Arg His Thr Cys Gly Ser Val Thr Gln
        115                 120                 125

<210> SEQ ID NO 56
<211> LENGTH: 138
<212> TYPE: PRT
<213> ORGANISM: Artificial sequence
<220> FEATURE:
<223> OTHER INFORMATION: Chimeric protein

<400> SEQUENCE: 56

Gly Ser His Met Thr Lys Lys Ala Ala Val Ser Glu Leu Leu Gln Ala
1               5                   10                  15

Ser Ala Pro Tyr Lys Ala Asp Val Glu Leu Cys Val Tyr Ser Thr Asn
            20                  25                  30

Glu Thr Thr Asn Cys Thr Gly Gly Lys Asn Gly Ile Ala Ala Asp Ile
        35                  40                  45

Thr Thr Ala Lys Gly Tyr Val Lys Ser Val Thr Thr Ser Asn Gly Ala
    50                  55                  60

```
Ile Thr Val Lys Gly Asp Gly Thr Leu Ala Asn Met Glu Tyr Ile Leu
 65                  70                  75                  80

Gln Ala Thr Gly Asn Ala Ala Thr Gly Val Thr Trp Thr Thr Thr Cys
                 85                  90                  95

Lys Gly Thr Asp Ala Ser Leu Phe Pro Ala Asn Phe Cys Gly Ser Val
            100                 105                 110

Thr Gln Leu Val Arg Ser Asp Tyr Lys Phe Tyr Glu Asp Ala Asn Gly
        115                 120                 125

Thr Arg Asp His Lys Lys Gly Arg His Thr
    130                 135

<210> SEQ ID NO 57
<211> LENGTH: 144
<212> TYPE: PRT
<213> ORGANISM: Artificial sequence
<220> FEATURE:
<223> OTHER INFORMATION: Chimeric protein

<400> SEQUENCE: 57

Gly Ser His Met Leu Val Arg Ser Asp Tyr Lys Phe Tyr Glu Asp Ala
 1               5                  10                  15

Asn Gly Thr Arg Asp His Lys Lys Gly Arg His Thr Gly Pro Ser Leu
             20                  25                  30

Lys Leu Thr Lys Lys Ala Ala Val Ser Glu Leu Leu Gln Ala Ser Ala
             35                  40                  45

Pro Tyr Lys Ala Asp Val Glu Leu Cys Val Tyr Ser Thr Asn Glu Thr
         50                  55                  60

Thr Asn Cys Thr Gly Gly Lys Asn Gly Ile Ala Ala Asp Ile Thr Thr
 65                  70                  75                  80

Ala Lys Gly Tyr Val Lys Ser Val Thr Thr Ser Asn Gly Ala Ile Thr
                 85                  90                  95

Val Lys Gly Asp Gly Thr Leu Ala Asn Met Glu Tyr Ile Leu Gln Ala
            100                 105                 110

Thr Gly Asn Ala Ala Thr Gly Val Thr Trp Thr Thr Thr Cys Lys Gly
        115                 120                 125

Thr Asp Ala Ser Leu Phe Pro Ala Asn Phe Cys Gly Ser Val Thr Gln
    130                 135                 140
```